United States Patent [19]
Vachtsevanos et al.

[11] Patent Number: 5,815,198
[45] Date of Patent: Sep. 29, 1998

[54] METHOD AND APPARATUS FOR ANALYZING AN IMAGE TO DETECT AND IDENTIFY DEFECTS

[76] Inventors: George J. Vachtsevanos, 2040 Dayron Ct., Marietta, Ga. 30062; Muid Mufti, 1041 State St., NW., Apartment 20, Atlanta, Ga. 30318; J. Lewis Dorrity, 3080 Beechwood Dr., Marietta, Ga. 30067

[21] Appl. No.: 657,023

[22] Filed: May 31, 1996

[51] Int. Cl.⁶ .................................................. H04N 7/18
[52] U.S. Cl. ............................... 348/88; 348/91; 348/92; 348/125; 348/128; 382/141
[58] Field of Search .................. 348/86, 87, 88, 348/91, 92, 125, 126, 128, 129, 130, 131; 382/118, 156, 190, 149, 141; H04N 7/18

[56] References Cited

U.S. PATENT DOCUMENTS

| | | | |
|---|---|---|---|
| 3,781,117 | 12/1973 | Laycak et al. | 356/200 |
| 3,803,420 | 4/1974 | Bossons | 250/562 |
| 3,972,624 | 8/1976 | Klein et al. | 356/200 |
| 4,110,048 | 8/1978 | Akutsu et al. | 356/200 |
| 4,173,441 | 11/1979 | Wolf | 356/431 |
| 4,298,808 | 11/1981 | Hill | 250/563 |
| 4,903,528 | 2/1990 | Balakrishnan et al. | 73/159 |
| 4,953,400 | 9/1990 | Bossuyt | 73/159 |
| 5,073,964 | 12/1991 | Resnikoff | 382/41 |
| 5,345,515 | 9/1994 | Nishi et al. | 382/8 |
| 5,457,539 | 10/1995 | Sturm | 356/429 |
| 5,471,991 | 12/1995 | Shinnar | 128/705 |
| 5,497,430 | 3/1996 | Sadovnik et al. | 382/156 |
| 5,513,275 | 4/1996 | Khalaj et al. | 348/126 |
| 5,544,256 | 8/1996 | Brecher et al. | 382/149 |
| 5,548,120 | 8/1996 | Parker et al. | 250/341.7 |
| 5,631,970 | 5/1997 | Hsu | 382/113 |

FOREIGN PATENT DOCUMENTS

| | | | |
|---|---|---|---|
| 3146738 | 6/1991 | Japan | D03D 41/00 |
| 6041851 | 2/1994 | Japan | D03D 51/18 |
| 6065844 | 3/1994 | Japan | D03D 51/18 |

OTHER PUBLICATIONS

Zadeh, L.A., "Fuzzy Sets," Information and Control 8, pp. 338–353, 1965.

Thyagarajan, K.S. and Chatterjee, S., "Fractal Scanning for Image Compression," Conference Record of The Twenty–Fifth Asilomar Conference on Signals, Systems & Computers, vol. 1 p. 467–471 1991.

Xuecheng, L., "Entropy, distance measure and similarity measure of fuzzy sets and their relations," Fuzzy Sets and Systems 52, pp. 305–318, 1992.

Phuvan, S., Oh, T.K., Caviris, N., Li, Y. and Szu, H, "Optoelectronic Fractal Scanning Technique for Wavelet Transform and Neural Net Pattern Classifiers" International Joint Conference on Neural Networks, pp. I–40–6, Jun. 7–11, 1992.

(List continued on next page.)

Primary Examiner—Tommy P. Chin
Assistant Examiner—Vu Le
Attorney, Agent, or Firm—Deveau, Colton & Marquis

[57] ABSTRACT

The Invention includes a method and apparatus which analyzes an image of an object to detect and identify defects in the object. The present invention utilizes a scanning technique which converts a 2-D image of the object into a 1-D image, a transformation technique which extracts relevant features from the image, and a fuzzy inferencing technique which utilizes the features generated by the transformation technique to detect and identify defects. The present invention preferably includes an off-line learning process which selects the optimum transform coefficients for a given set of defects and stores the corresponding features in a rulebase. Preferably, the wavelet transform is used as the transformation technique to provide an analysis of the image which is localized in the frequency and time domains. The present invention may also include an on-line learning process when the present invention is incorporated into a manufacturing process for real time inspection of the object being manufactured. The on-line learning process attempts to nullify the effects of noise which may be associated with the image sensors being used to read the image by using a similarity function to maintain a predetermined level of fuzziness of the inference engine of the present invention.

24 Claims, 29 Drawing Sheets

OTHER PUBLICATIONS

Szu, H.H. Telfer, B. and Kadambe, S., "Neural network adaptive wavelets for signal representation and classification," Optical Engineering, vol. 31, No. 9, pp. 1907–1916, Sep. 1992.

Kang, H. and Vachtsevanos, G., "Fuzzy Hypercubes: Linguistic Learning/Reasoning Systems for Intelligent Control and Identification," Journal of Intelligent and Robotic Systems 7, pp. 215–243, 1993.

Bakshi, B.R., Koulouris, A. and Stephanopoulos, G., "Wave–Nets: novel learning techniques, and the induction of physically interpretable models," The International Society for Optical Engineering, vol. 2242, pp. 637–648, 1994.

Mufti, M. and Vachtsevanos, G., "An Intelligent Approach to Fault Detection and Identification," Proceedings of the 1995 American Control Conference, vol. 3, pp. 1621–1622, Jun. 1995.

Kang, H. and Vachtsevanos, G., "Fuzzy Hypercubes: A Possibilistic Inferecning Paradigm," IEEE Conf. on Fuzzy Systems, vol. 1, pp. 553–560, 1992.

Kang, H. and Vachtsevanos, G.J., "Model Reference Fuzzy Control," Proc. of 27th IEEE Conf. on Decision and Control, pp. 751–756, Dec. 1989.

RASTER SCANNING

COMPLETELY MISSED
HORIZONTAL FEATURE

LOSS OF ADJACENCY
IN VERTICAL DIRECTION

FRACTAL SCANNING

FEATURE CAPTURED IN ANY DIRECTION

Basic Fractal

Orientation 0

| Chromosome    | 1 | 2  | 3  | 4  | 5  | 6  | 7  | 8  | 9  | 10 |
|---------------|---|----|----|----|----|----|----|----|----|----|
| Fitness       | 8 | 2  | 17 | 7  | 2  | 12 | 11 | 7  | 3  | 7  |
| Running Total | 8 | 18 | 27 | 34 | 36 | 48 | 59 | 66 | 69 | 76 |

| Random Number     |  |  | 23 | 49 | 76 | 13 | 1 | 27 | 57 |
|-------------------|--|--|----|----|----|----|---|----|----|
| Chromosome Chosen |  |  | 3  | 7  | 10 | 3  | 1 | 3  | 7  |

FIG. 11

| Parent 1: | 1 0 \| 0 1 1 \| 0 1 0 | Child 1: | 1 0 0 0 0 0 1 0 |
|---|---|---|---|
| Parent 2: | 1 1 \| 0 0 0 \| 1 1 1 | Child 1: | 1 1 0 1 1 1 1 1 |
| Parent 1: | 1 0 0 \| 1 1 0 1 \| 0 | Child 1: | 1 0 0 0 0 1 1 0 |
| Parent 2: | 1 1 0 \| 0 0 1 1 \| 1 | Child 1: | 1 1 0 1 1 0 1 1 |

FIG. 12

| $j$ | $a_1$ | $a_2$ | ... | $a_n$ | $D(a_k^j)$ | $a_1$ | $a_2$ | ... | $a_n$ | $D(a_k^j)$ | Fitness |
|---|---|---|---|---|---|---|---|---|---|---|---|
| 1 | $d_{k,a_1}^1$ | $d_{k,a_2}^1$ | ... | $d_{k,a_n}^1$ | $D_k^1$ | $s_{k,a_1}^1$ | $s_{k,a_1}^1$ | ... | $s_{k,a_1}^1$ | $I_k^1$ | $F(S^1)$ |
| 2 | $d_{k,a_1}^2$ | $d_{k,a_2}^2$ | ... | $d_{k,a_n}^2$ | $D_k^2$ | $s_{k,a_1}^2$ | $s_{k,a_1}^2$ | ... | $s_{k,a_1}^2$ | $I_k^2$ | $F(S^2)$ |
| ⋮ | ⋮ | ⋮ | ⋱ | ⋮ | ⋮ | ⋮ | ⋮ | ⋱ | ⋮ | ⋮ | ⋮ |
| $P$ | $d_{k,a_1}^P$ | $d_{k,a_2}^P$ | ... | $d_{k,a_n}^P$ | $D_k^P$ | $s_{k,a_1}^P$ | $s_{k,a_1}^P$ | ... | $s_{k,a_1}^P$ | $I_k^P$ | $F(S^P)$ |

FIG. 13

Performance level of system on the given defects.

| Defect name | Actual number | Number detected/identified |
|---|---|---|
| Mispicks | 12 | 12 |
| Start Mark | 4 | 3 |
| End out | 4 | 4 |
| Slub | 6 | 6 |
| Oil | 1 | 1 |
| No defect | 19 | 19 |

FIG. 29

METHOD AND APPARATUS FOR ANALYZING AN IMAGE TO DETECT AND IDENTIFY DEFECTS

BACKGROUND OF THE INVENTION

1. Technical Field of the Invention

The present invention provides a method and apparatus for analyzing an image to detect and identify defects and, more particularly, to a method and apparatus which combines fractal scanning, wavelet transformation, fuzzy logic and off-line and on-line learning to provide a robust fault detection and identification (FDI) system which detects and identifies faults or defects in an object being manufactured or processed, such as textiles, glass, lumber, pulp, metals, paper, food, etc., and which controls the manufacturing or processing in accordance with the types of defects identified to eliminate or minimize the defects.

Fault detection and identification (FDI) is an important part of modern control strategy. FDI algorithms generally consist of two portions, namely, a detection portion and an identification portion. Fault detection is the process of deciding whether any one of the anticipated faults or defects has occurred. Once the presence of the defects has been established, fault identification distinguishes which particular defect has occurred. There are a number of systems where traditional FDI techniques are not applicable due to the unavailability of analytic models. FDI becomes more difficult when there is a large variation in signal time constants. A high degree of system interdependencies, process and measurement noise, large-grain uncertainty and randomness make FDI even more challenging. The present invention provides an FDI algorithm for such systems. With these types of systems, proper signal analysis is of primary importance. Analysis only in the time or frequency domains generally is not sufficient to capture the faults that occur over a wide band of frequencies. Analysis of these types of faults should be localized in both the time and frequency domains. For this reason, the present invention proposes using a transform known as the wavelet transform which is an excellent signal analysis and decomposition tool for such systems because it provides an analysis which is localized in both the frequency and time domains.

In view of the behavior of these types of systems, the present invention proposes a solution which combines wavelet transform and fuzzy inferencing techniques. This novel arrangement, hereinafter called Fuzzy Wavelet Analysis (FWA), provides a system capable of analyzing the fault signatures in a time(or space)/frequency localized manner with the ability to accommodate uncertainty. Preferably, on-line and off-line learning are implemented by the present invention for maximizing the performance of the FDI system of the present invention. Development of FWA as an intelligent paradigm provides on-line adaptability and FDI process improvement through learning. The off-line learning process of the present invention is achieved by maximizing the detectability and identifiability measures, which can be calculated from analytic formulas and which are the primary constraints for designing knowledge-based systems. The on-line learning process of the present invention involves parametric adjustment of the fuzzification process so as to minimize the sensitivity of the FDI system to noise. Thus, a new similarity measure is defined which has a nonlinear adjustment of the input sensitivity.

The FWA of the present invention generally involves analysis of 1-D data. However, it can be applied to 2-D images by using specialized scanning techniques at the preprocessing stage. Analysis of images for the purpose of FDI requires information in both the horizontal and vertical directions to acquire maximum information about the features in the image. However, analysis in 2-D is computationally intensive and time consuming. Hence, a better approach is to scan the image into a 1-D stream of data. Unfortunately, commonly used scanning techniques which scan the image into a 1-D data stream, such as raster scanning, do not preserve the adjacency of the features in the direction perpendicular to the direction of scanning. Feature extraction for FDI is easier in 1-D scanning techniques that retain the neighborhood relationship of the image. Thus, a technique that scans one area of the image completely before moving to the next area is desirable. In accordance with the present invention, a fractal scanning technique is used which is much more efficient at capturing features in digital images than other scanning techniques.

2. Prior Art

Current trends in industrial and manufacturing automation have placed an increased emphasis on the need for quality and reliability, both in the process control and product characterizations areas. As the technologies are becoming more complicated, failure free and reliable processes are becoming vital. Automatic control systems are becoming more complex as they are called upon to regulate critical dynamic systems and the associated control algorithms and control actuators entail more sophistication. Consequently, there is a growing demand for fault tolerance, which can be achieved not only by improving the reliability of the functional units but also by efficient FDI concepts. Fault detection and identification is of interest in a wide variety of applications such as control systems, image analysis, analysis of radar signals, smart sensors, texture analysis, medicine, industry, etc.

From the perspective of product characterization, one aspect of quality is perceived as a defect-free final product. Product inspection and defect classification is one of the key issues in the manufacturing arena. Manual inspection or traditional signal processing have proven to be inadequate in many applications. This is due to the presence of a high degree of uncertainty and complexity in these systems. Intelligent processing tools like fuzzy logic, neural networks and intelligent optimization techniques are currently being used which accommodate large grain uncertainty while utilizing all the information about the system when the information from analytic models of the system is not adequate. This gives intelligent FDI schemes an advantage over conventional FDI techniques, which rely primarily on analytic models. However, heretofore such systems have been analyzed in the time and/or frequency domains. Due to the wide range of time constants, analysis of such systems in the frequency domain alone would mask the sudden bursts of high frequency. Unless the frequency domain resolution is very fine, slowly varying fault features can be masked in the dc bias. Likewise, analysis in the time domain would not reflect the periodicity of the features. Hence, analysis only in the frequency or time domain generally is not sufficient to capture features that are spread in a wide band of frequencies. In accordance with the present invention, this problem is overcome by using Wavelet Transform (WT) techniques which provide an analysis which is localized in both the frequency and time domains. WT uses a variable window size to analyze different frequencies. Moreover, it provides a wide choice of wavelets for providing the best fit for a given application.

Over the last two decades, basic research in FDI has gained increased attention, mainly due to trends in automation, the need to address complex tasks, and the corresponding demand for higher availability and security of the control systems. However, a strong impetus has also come from the side of modern control theory that has brought forth powerful techniques in mathematical modeling, state estimation and parameter identification.

In general, FDI schemes can be classified broadly as: (1) model based FDI techniques; and (2) knowledge based FDI techniques. Model-based techniques (analytic) generally use the information of the state variables from the model of the system to predict the future values. A disparity between the actual values and the predicted values suggests a possible fault. This is a very robust approach to FDI for systems where accurate models are available. Knowledge-based approaches provide a very useful alternative in systems where accurate models are not available.

Model-based FDI techniques have been thoroughly tested and verified to perform satisfactorily in many applications. Based upon the methods of using the model, various approaches have been developed. For example, innovation-based techniques, such as Generalized Likelihood Ratio, are used for linear stochastic systems. This technique requires N+1 hypothesis testing: $H_i$ for the occurrence of fault i, i=1, . . . , N, and $H_o$ for no failure. The failure decision is based upon the maximum likelihood ratio of the conditional probabilities for $H_i$ and $H_o$. A technique known as the Failure Sensitive Filters technique employs a class of filters wherein the primary criterion for the choice of the filter is that the effects of certain faults are accentuated in the filter residue. However, it is not always possible to design a filter that is sensitive only to a particular fault. Furthermore, a performance trade off is inherent in this method; as the sensitivity of the filter to new data is increased, by effectively increasing the bandwidth of the filter, the system becomes more sensitive to sensor noise and the performance of the detection algorithm under no-failure conditions degrades.

Another technique known as the Multiple Hypothesis Filter Detectors technique uses a bank of filters (one for each fault mode) and each filter is used to calculate the conditional probability that each failure mode has occurred. This technique generally is not very popular due to its level of complexity, which increases exponentially as the system expands.

The Parity Space Approach exploits the inconsistency of data (due to failure) coming from different sources of the system. The Direct Redundancy or Hardware Redundancy technique uses the instantaneous values of different sensors while the Temporal Redundancy technique uses a dynamic relationship between sensor outputs and actuator inputs over a period of time. The Hardware Redundancy technique is simple and easy to apply. However, it requires multiple sensors for each variable. Another drawback of this technique is that it works on the assumption that only one sensor fails at a time (in a three sensor arrangement). Analytic Redundancy uses data from sensors representing different parameters of the system that can be mathematically related by the model or part of the model.

With the availability of mathematical and computational tools, the trend in FDI research has shifted toward analytical (i.e., functional) rather than physical redundancy. This implies that the inherent redundancy contained in the dynamic relationships among the system inputs and measured outputs is exploited for FDI. In such approaches, one makes use of a mathematical model of the system or models describing certain modules of the overall system.

All of the known techniques described above utilize a model of the system (or part of the system) for fault analysis. These techniques work satisfactorily as long as the model characteristics approximate the actual system. However, their performance degrades rapidly if the model does not closely represent the actual system. Unfortunately, accurate models are not available for most systems. There is a growing potential for using knowledge-based models and algorithms instead of analytic ones. This approach is, of course, the only one available in cases where analytic models are not available. A comparison of a model-based technique and a knowledge-based technique is shown in FIG. 1. It can be seen in FIG. 1 that the knowledge base replaces the model in the overall architecture. This knowledge-based approach has created a new dimension of possible fault diagnosis techniques for complex processes with incomplete process knowledge. Whereas the analytic methods use quantitative analytical models, the expert systems approach makes use of qualitative models based on the available knowledge of the system. Although the intelligent FDI techniques do not require an accurate analytic model, they are restricted to identification of only predetermined defects. This is, however, acceptable in many cases as the fault modes in most applications are already known.

Most of the intelligent techniques being used today employ a learning mechanism (on-line or off-line) which uses information obtained from an expert, historical data, extrinsic conditions, etc. The learning procedure, in most cases, is cast as an optimization problem which adjusts the parameters of the detection algorithm, modifies the knowledge-base, initiates mode switching, etc. For example, it is known to use learning to determine the optimum weights for aggregation of information from different sources for vibration monitoring. Neural-net based FDI techniques are known which use learning to adjust the weights of individual neurons. Fuzzy Associative Memories (FAMs) are known which employ learning to design an inferencing hypercube.

The fault identification problem is in fact the classification of faults into different categories. It may be viewed as a mapping from the feature space to the decision space. One well known fuzzy classification routine is the Fuzzy C-Means (FCM) algorithm derived from its crisp version called ISODATA. Consider the partitioning of the set $X=\{x_1, x_2, \ldots, x_n\}$ into c-partitions, $c \in N$. FCM assigns a degree of association $\mu_{ik}$ of the kth feature with the ith partition (fault mode in our case). For the cluster center $\tau_i$ of the ith cluster, FCM estimates $\mu_{ik}$ as follows $$\min z = \sum_{i=1}^{c} \sum_{k=1}^{n} (\mu_{ik})^m \|x_k - v_i\|^2$$

These types of approaches work on the assumption that the fuzzy classes are fully understood by the user and that there exists sufficient knowledge of the associated features. They do not allow the classes to be self generated or evolved over time. Hence, they lack the element of learning that would enable the system to work independently without user assistance.

It is also known to use a multi-level architecture for classification tools based on fuzzy logic. The highest level is the application level, the middle level provides the definition of a language for the specification and reasoning, and the lowest level contains the elementary data structure definition and operators for classification and reasoning.

Other popular methods for classification use a fuzzy rule-base, a fuzzy decision hypercube and fuzzy relational matrix. All of these techniques rely upon the user to provide the expert knowledge for the inference engine. Unfortunately, the generation of a fuzzy decision hypercube or FAM is not very simple for most applications.

The FWA technique of the present invention attempts to overcome shortcomings of the existing methods of fault detection and identification. This technique provides a unified platform for process fault diagnosis and product characterization. Prior to performing FWA, the present invention implements fractal scanning which converts 2-D image information into a 1-D data stream by scanning the image in fractal patterns. The wavelet transform is then applied to provide an analysis of the image which is localized in both the time and frequency domains. The FWA technique then utilizes the fault features generated by the wavelet transforms to detect and identify defects and optimizes features extracted from the various faults for use in the knowledge-base. This requires off-line learning. Preferably, both off-line and on-line learning are implemented by the FDI system of the present invention.

In accordance with a preferred embodiment of the present invention, FWA is applied in real time to a textile manufacturing process to detect and identify faults occurring in textile fabrics being manufactured and to control the textile manufacturing process to eliminate or minimize the faults.

BRIEF SUMMARY OF THE INVENTION

In accordance with the present invention, a method and apparatus is provided which analyzes an image of an object to detect and identify defects in the object. The present invention utilizes a scanning technique which converts a 2-D image of the object into a 1-D image, a transformation technique which extracts relevant features from the scanned image, and a fuzzy inferencing technique which utilizes the fault features generated by the transformation technique to detect and identify defects. The present invention preferably includes an off-line learning process which selects the optimum transform coefficients for a given set of defects and stores the corresponding features in a rulebase. Preferably, the wavelet transform is used as the transformation technique to provide an analysis of the image which is localized in the frequency and time domains. The present invention may also include an on-line learning process when the present invention is incorporated into a manufacturing process for real time inspection of the object being manufactured. The on-line learning process attempts to nullify the effects of noise which may be associated with the image sensors being used to read the image by using a similarity function to maintain a predetermined level of fuzziness of the inference engine of the present invention.

Accordingly, it is an object of the present invention to provide a robust fault detection and identification system.

It is another object of the present invention to provide a fault detection and identification system which combines fractal scanning, a wavelet transform technique and fuzzy logic to extract fault features which are used to detect and identify defects and which are optimized for use in a knowledge-base for off-line learning.

It is yet another object of the present invention to provide a fault detection and identification system which can be incorporated as part of a manufacturing line for real time detection and identification of defects occurring in an object being manufactured and for controlling the manufacturing process to improve the production quality of the object being manufactured.

It is yet another object of the present invention to provide a fault detection and identification system which combines fractal scanning, a wavelet transform process, fuzzy logic and off-line and on-line learning to provide a robust fault detection and identification system which maximizes defect detection and identification while minimizing false detection of defects.

It is yet another object of the present invention to provide an intelligent fault detection and identification system which can be incorporated into a textile fabric manufacturing process for detecting defects in fabric being manufactured and for controlling the manufacturing process to eliminate or minimize defects in the fabric.

It is yet another object of the present invention to provide a robust fault detection and identification system which is economical.

These and other objects of the present invention will become apparent from the following description, drawings and claims.

BRIEF DESCRIPTION OF THE DRAWING

FIG. 5b illustrates the 5×5 dimension of the fractal of FIG. 5a.

FIG. 11 is a table showing the results of using Roulette Wheel Parent Selection for implementing the genetic algorithm preferably used in the off-line learning module of the present invention.

FIG. 12 illustrates examples of two-point crossover of the genetic algorithm.

FIG. 13 is a table containing calculations relating to detectability which are made by implementation of the genetic algorithm.

FIG. 29 illustrates the results of the experimental run.

DETAILED DESCRIPTION OF THE INVENTION

As stated above, the present invention preferably combines fractal scanning, a wavelet transform process, fuzzy logic and on-line and off-line learning to provide a robust fault detection and identification (FDI) system. Therefore, each of these components will be discussed in detail separately. Finally, a discussion will be provided of the preferred embodiment of the present invention wherein the fuzzy wavelet analysis (FWA) of the present invention is applied to textile fabric inspection.

1. Fractal Scanning

The FWA of the present invention generally involves analysis of 1-D data. However, it can be applied to 2-D images by using specialized scanning techniques at the preprocessing stage. Analysis of images for the purpose of FDI requires information in both the horizontal and vertical directions to acquire maximum information about the features in the image. However, analysis in 2-D is computationally intensive and time consuming. Hence, a better approach is to scan the image into a 1-D stream of data. Unfortunately, commonly used scanning techniques which scan the image into a 1-D data stream, such as raster scanning, do not preserve the adjacency of the features in the direction perpendicular to the direction of scanning. Feature extraction for FDI is easier in 1-D scanning techniques that retain the neighborhood relationship of the image. Thus, a technique that scans one area of the image completely before moving to the next area is desirable. In accordance with the present invention, a fractal scanning technique is used which is much more efficient at capturing features in digital images than other scanning techniques.

Fractal scanning is very suitable for the purpose of fault detection because of the inherent scaling and nesting properties of fractals. The following attributes of fractal scanning make it ideal for this application: (1) fractal scanning is nested recursively in a self similarity manner; (2) it moves in all directions of interest within the lowest dimension of the image; (3) it preserves the adjacency of the image features in all directions; (4) it is scaleable to the required resolution due to the fractional dimension; (5) it allows for a substantial reduction in data; (6) it assists in reducing the amount of calculations; and (7) it enables the availability of 1-D instead of 2-D data.

Unfortunately, thus far none of the studies involving fractal scanning have given a systematic and organized algorithm for generating the fractal scan. In accordance with the present invention, a detailed mathematical representation of a fractal scanning technique has been developed and is presented here which provides a very reliable and efficient scanning technique for fault detection.

Figure 1:
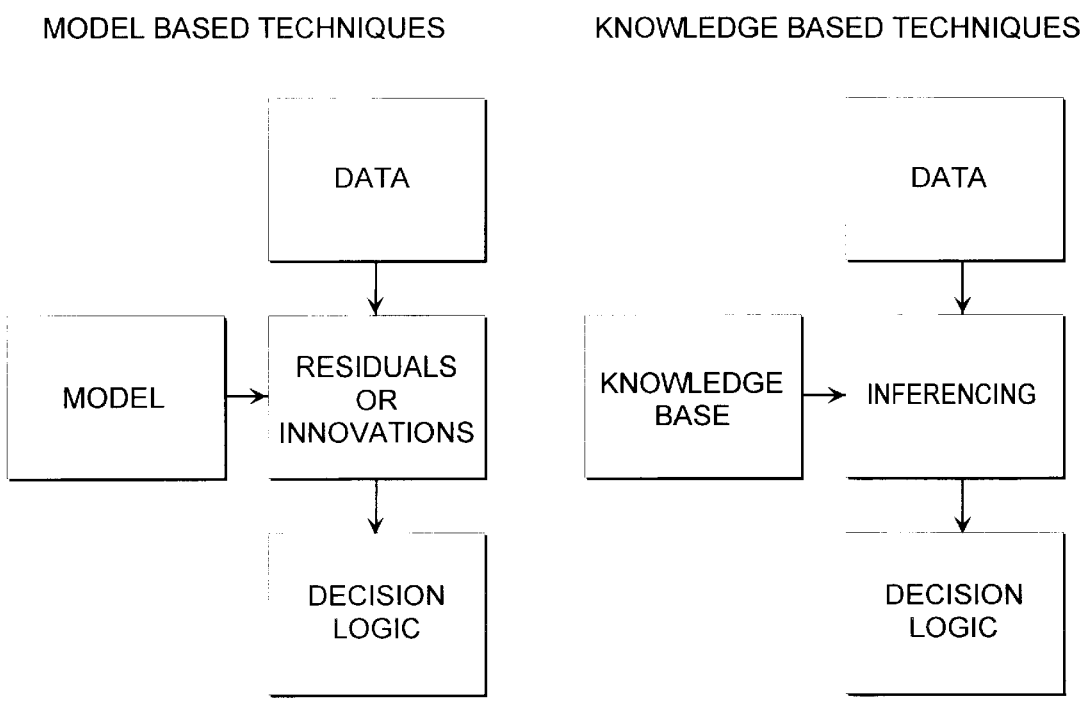
FIG. 1 is a block diagram comparing model-based FDI techniques to knowledge-based FDI techniques.
Figure 2:
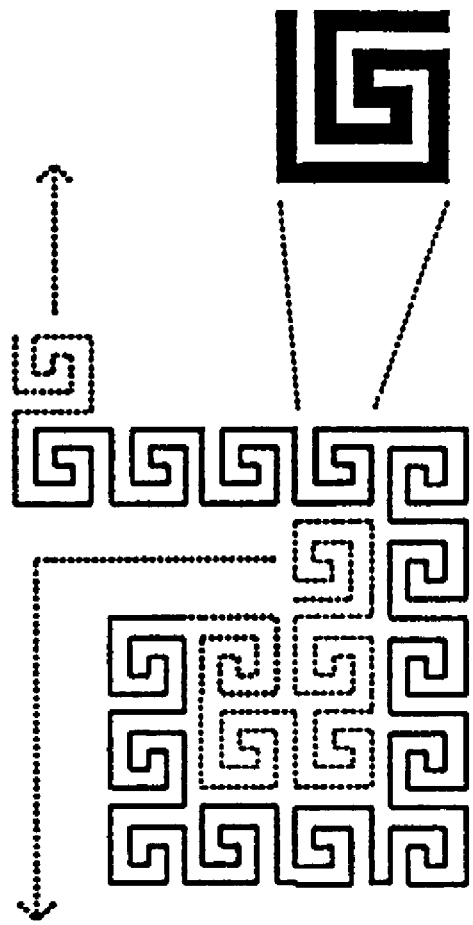
FIG. 2 illustrates the nested hierarchy of a two-level fractal.
Figure 3:
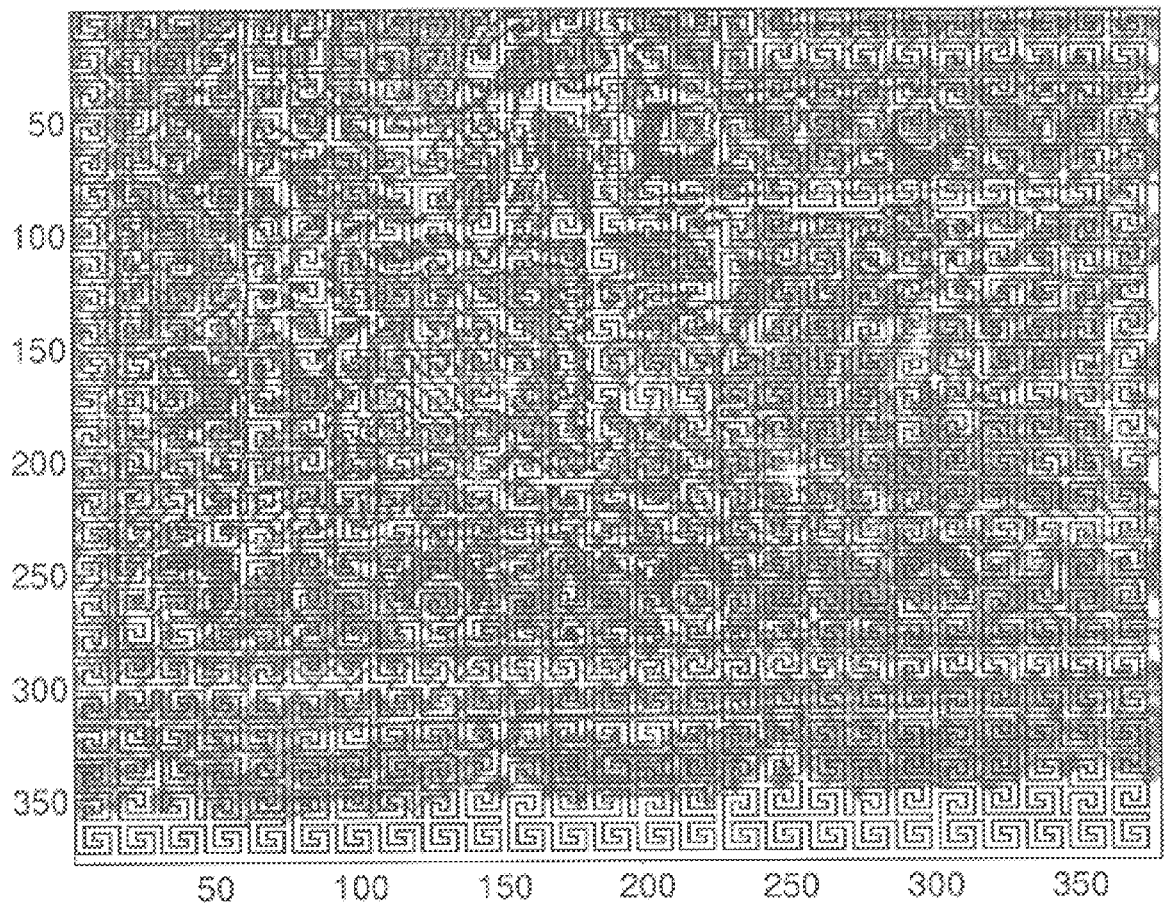
FIG. 3 illustrates a complete fractal scan over an image of a carpet.

The ability of the fractal scan to capture the faults of smallest dimension comes from the self similarity nesting property of the fractals. Each fractal is composed of self similar fractals of smaller size and so on. The recursion continues until the size of the fractal is comparable to the size of the smallest anticipated fault. The nested hierarchy of a two level fractal is shown in FIG. 2. The final fractal is one continuous line whose length depends upon the dimension of the fractal. An example of the complete fractal scan over the image of a carpet is shown in FIG. 3.

Figure 4:
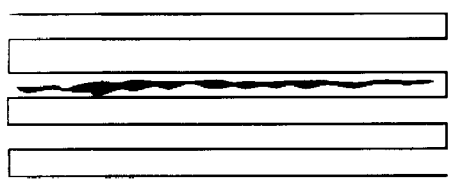
FIG. 4 illustrates the advantages of fractal scanning over raster scanning for fault detection.
Figure 4:
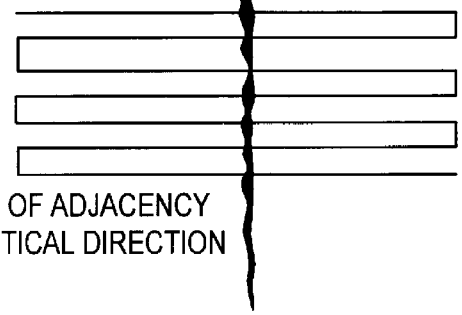
Figure 4:
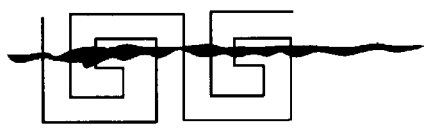
Figure 4:
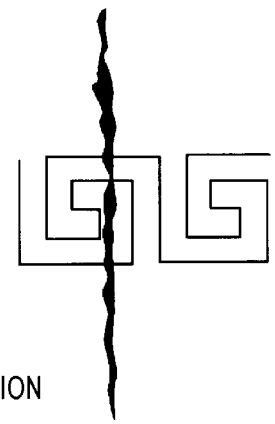

As mentioned above, the fractal scanning technique preserves the neighborhood relationship in an image. The intricate geometry of a fractal provides the liberty to scan less than the total number of pixels without loss in detectability of the methodology. This introduces the scale factor s which represents the number of pixels omitted between two lines. The problem with conventional scanning, such as raster scanning, is that it can completely miss a fault feature in the horizontal direction if the dimension of the fault in the vertical direction is less than s. On the other hand, if a fault occurs in the vertical direction, the vertical adjacency of the feature is lost as the scan goes all the way to the end of the image and comes back to read the feature again. Hence, a very critical sequence of pixel intensities can be lost as these pixels occur too far apart in the data stream. Both of these scenarios are shown in FIG. 4. It can be seen from FIG. 4 that the likelihood of missing a fault is low when using the fractal scanning technique. Moreover, the proximity relationship is better retained as compared to the conventional scanning techniques. The fractal scan crosses the fault at a number of places which are in close proximity to each other.

Figure 5A:
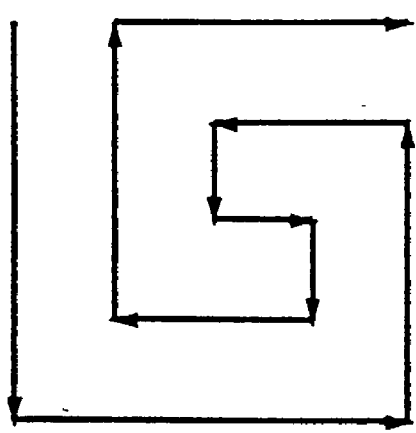
FIG. 5a illustrates the preferred basic fractal of the present invention.

FIG. 5a illustrates the preferred basic fractal used for this algorithm. It will be apparent to those skilled in the art that fractals different from the one shown here can also be used depending upon the nature of the application. This shape of the fractal is particularly suited for textile fabric inspection due to the orthogonal nature of the faults in textile fabrics, to which FWA is applied in accordance with the preferred embodiment.

Figure 5B:
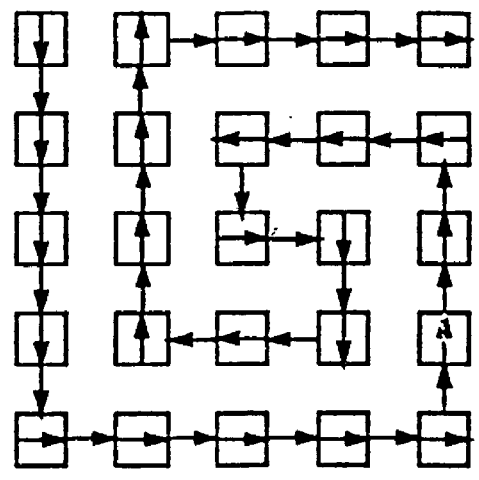

To provide an example of a mathematical representation of the fractal, a basic fractal is resolved over a 5×5 grid as shown in FIG. 5b. Each box on the grid is itself a similar fractal repeating itself with a different orientation, θ, given by the direction of the arrow. It is seen that the fractal in FIG. 5a starts from the top left corner and ends at the top right corner. The net displacement can be represented by the direction vector (1,0). Hence the orientation of this fractal is at an angle of 0 radians. It can be seen that the orientation of the sub-fractals in FIG. 5b is one of the following angles:

$$0, \frac{\pi}{2}, \frac{2\pi}{2}, \frac{3\pi}{2}$$

or $$\theta_n = \frac{n\pi}{2} \quad n = 0, 1, 2, 3$$

The representation n=4, 5, . . . are mapped back to the principal argument (n=0, 1, 2, 3). Therefore the definition of only these four orientations is necessary to accomplish the connectivity of the whole fractal.

Let a fractal be represented by $f^r_{n}$, where r=0, 1, 2 ..., L, is the level of the fractal in the nested hierarchy. L is the total number of levels. A larger value of r represents a fractal of larger physical dimension. n∈{0, 1, 2, 3} represents the orientation of the fractal given by the angle nπ/2. The nested arrangement for a fractal with orientation n and level r is given by an ordered set as shown below:

$$f_n^r = (f_{n_1}^{r-1}, f_{n_2}^{r-1}, f_{n_3}^{r-1}, \ldots, f_{n_K}^{r-1}) \quad \text{Equation 1}$$

where $n_1, \ldots, n_k$ are the orientation for sub-fractals in the sequence they are connected and K is the number of sub-fractals in one fractal (25 in this case).

The orientation of the sub-fractals for the basic fractal are obtained from FIG. 5b. Starting from the top left corner, the first box has an orientation of $$\frac{3\pi}{2} \text{ or } n = 3.$$

Hence the first subfractal of the basic fractal $f^L_0$ is $f^{L-1}_3$. Moving along in the direction of the arrow, the next box is also pointing down which refers to $f^{L-1}_3$. Continuing the same argument, the third and the fourth subfractals have the same direction and the fifth one has direction 0. This implies a sub-fractal $f^{L-1}_0$. Likewise, completing the directions of all the 25 sub-fractals, the representation of the basic fractal becomes:

$$f_0^L = (f_3^{L-1}, f_3^{L-1}, f_3^{L-1}, f_3^{L-1}, f_0^{L-1}, f_0^{L-1}, f_0^{L-1}, f_0^{L-1}, f_0^{L-1},$$
$$f_1^{L-1}, f_1^{L-1}, f_2^{L-1}, f_2^{L-1}, f_2^{L-1}, f_0^{L-1}, f_3^{L-1}, f_3^{L-1}, f_2^{L-1}, f_1^{L-1},$$
$$f_1^{L-1}, f_1^{L-1}, f_1^{L-1}, f_0^{L-1}, f_0^{L-1}, f_0^{L-1}) \quad \text{Equation 2}$$

For simplicity, the fractals are associated with direction set θ. For the basic fractal, the direction set is given as:

$$\theta_o = (3,3,3,3,0,0,0,0,0,1,1,2,2,2,0,3,3,2,1,1,1,1,0,0,0) \quad \text{Equation 3}$$

The elements of the direction set $\theta_n$ are represented by $\xi^n_i \in \{0, 1, 2, 3\}$, and are related to the direction $\theta_{\xi_i}$ of a sub-fractal by:

$$\xi_i = \frac{\theta_{\xi_i}}{\pi/2} \quad i = 1, \ldots, 25 \quad \text{Equation 4}$$

Once the representation of the basic fractal is complete, fractals with other orientations can be generated. As stated above, only four orientations, given by $$\theta = 0, \frac{\pi}{2}, \frac{2\pi}{2}, \text{ and } \frac{3\pi}{2},$$

are required. All these orientations can be derived from the basic fractal. In general, a mapping from any orientation to another one can be calculated. For (m,n)=(0,1), (1,0), (2,3), (3,2), $f_o \leftrightarrow f_1$, $f_2 \leftrightarrow f_3$ are reflections across the line y=x in the xy-plane. If $$\theta_n = \frac{n\pi}{2}$$

is the angle at which a fractal is oriented, represented by (cos $\theta_n$, sin $\theta_n$), then mapping $f^r_n \to f^r_m$ is given by:

$$(\cos\theta_m \; \sin\theta_m) = (\cos\theta_n \; \sin\theta_n) \begin{pmatrix} 0 & 1 \\ 1 & 0 \end{pmatrix} \quad \text{Equation 5}$$

$$\theta_m = \tan^{-1}\left(\frac{\cos\theta_n}{\sin\theta_n}\right)$$

$$\theta_m = \theta_n + \frac{\pi}{2}(-1)^n, (m,n) = (0,1), (1,0), (2,3), (3,2)$$

Similarly the transformation for (m,n)=(1,2), (2,1), (3,0), (0,4), respectively, is the reflection across the line y=−x. The transformation matrix is $$\begin{pmatrix} 0 & -1 \\ -1 & 0 \end{pmatrix} \quad \text{Equation 6}$$

which gives $$\theta_m = \theta_n - \frac{\pi}{2}(-1)^n, (m,n) = (1,2), (2,1), (3,0), (0,4)$$

The transformation for (m,n)=(0,2), (2,0), (1,3), (3,1), respectively, is two successive reflections shown above. The transformation matrix in this case is $$\begin{pmatrix} 0 & 1 \\ 1 & 0 \end{pmatrix} \begin{pmatrix} 0 & -1 \\ -1 & 0 \end{pmatrix} = \begin{pmatrix} -1 & 0 \\ 0 & -1 \end{pmatrix} \quad \text{Equation 7}$$

and $$\theta_m = \theta_n - \pi(-1)^n, (m,n) - (0,2), (2,0), (1,3), (3,1)$$

Combining the conditions of Equations 4, 5 and 6, we arrive at:

$$\theta_m = \theta_n + \frac{\pi}{2}(n-m)(-1)^{n+m} \quad \text{Equation 8}$$

which suggests $$\xi_i^m = \xi_i^n + (n-m)(-1)^{\xi_i^n + \xi_i^m} \quad \text{Equation 9}$$

where $\xi^m_i \in \theta_m$ and $\xi^n_i \in \theta_n$. The mapped orientations of the direction sets, $\theta_1, \theta_2, \theta_3$ from 74$_0$ are as follows:

$$\theta_1 = (2,2,2,2,1,1,1,1,1,0,0,3,3,3,1,2,2,3,0,0,0,0,1,1,1) \quad \text{Equation 10}$$

$$\theta_2 = (1,1,1,1,2,2,2,2,2,3,3,0,0,0,2,1,1,0,3,3,3,3,2,2,2) \quad \text{Equation 11}$$

$$\theta_3 = (0,0,0,0,3,3,3,3,3,2,2,1,1,1,3,0,0,1,2,2,2,2,3,3,3) \quad \text{Equation 12}$$

Figure 6:
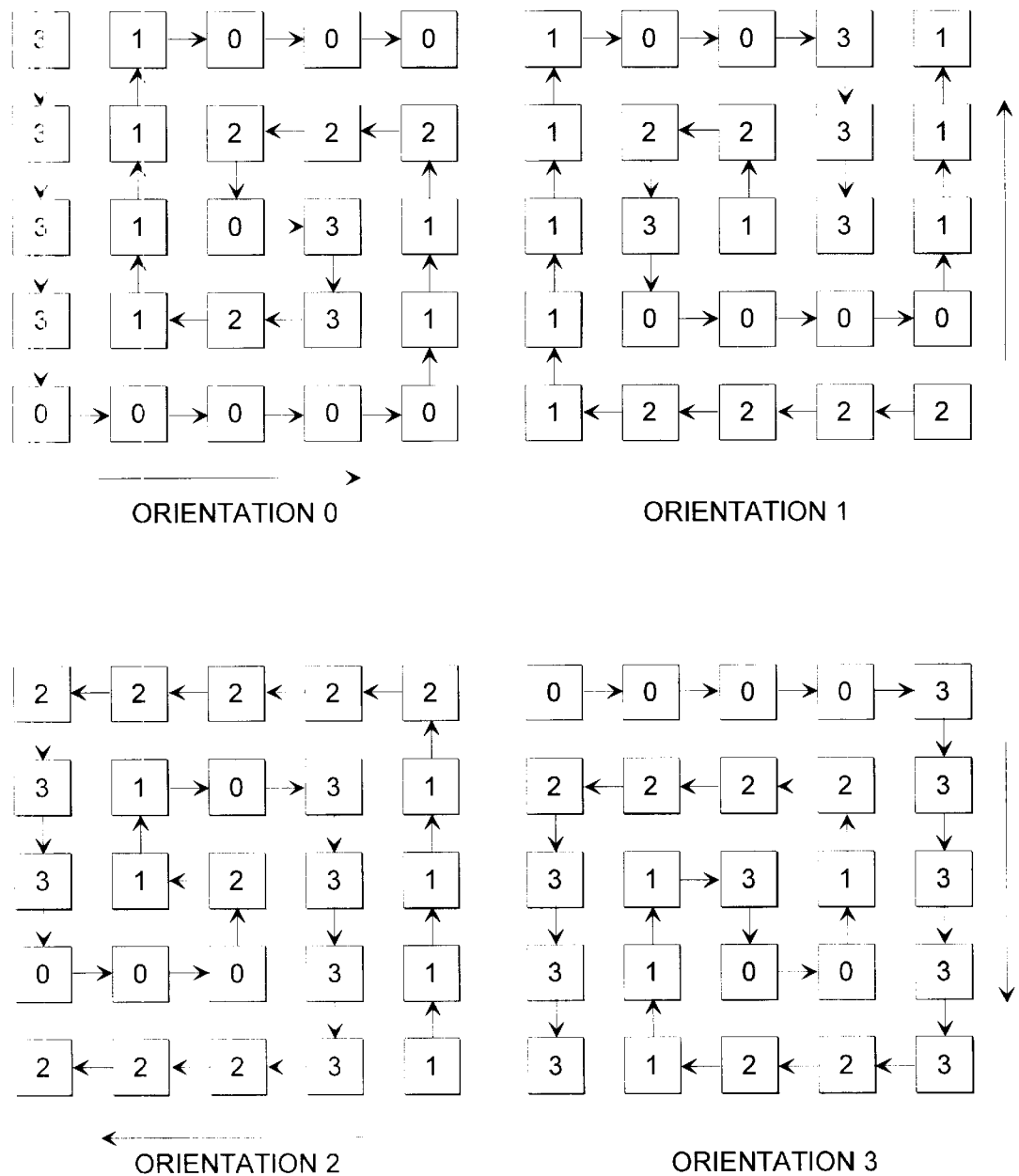
FIG. 6 illustrates different orientations of basic fractals.

These four orientations are shown in FIG. 6. The smaller boxes represent the nested fractals with their individual orientations.

Two fractals of particular orientation can be connected to form a continuous line by a unique link. The direction of a link between $\xi_i$ and $\xi_j$ is given by $d(\xi_i, \xi_j)$, $$d(\xi_i, \xi_j)) = \frac{3 - \left(1 - 2\left[\frac{\xi_i}{2}\right]\right)|2\xi_j - 3|}{2} \quad \text{Equation 13}$$

where $$\left[\frac{\xi_i}{2}\right]$$

represents the integral part of the fraction. This directional link is shown by the arrows between the boxes in FIG. 5b. The directional link is essential for the physical connectivity of the scan.

In accordance with the present invention, a marked increase in the efficiency of the fault detection algorithm has been obtained by using fractal scanning. The increase in performance is as follows: (1) fractal scanning reduces both the amount of data and the calculation effort; (2) for a scale factor of 2, data is immediately reduced to one-half, (3) as an example, detection of an edge in a 2-D image using a Sobel operator requires 9+9=18 multiplications and 2 additions; a similar edge detection that employs a fractal scan requires 3 multiplications and 1 addition; (4) recursive algorithms for a fractal scan results in increased efficiency, and (5) the 1-D data provide information about both the horizontal and the vertical directions.

2. Wavelet Transform

Wavelet theory provides a unified framework for a number of techniques which had been developed for various signal analysis and processing applications. Wavelet Transform (WT) is of interest as it provides an alternative to the classical Short Time Fourier Transform (STFT) and Gabor Transform for non-stationary signal analysis. The basic difference is that, in contrast to STFT, which uses a single analysis window, the WT uses short windows at high frequencies and a long window at low frequencies. This is the essence of the so-called "constant-Q" or constant relative bandwidth frequency analysis. Basis functions, called wavelets, are the underlying element of the wavelet analysis. They are obtained from a single prototype wavelet by dilations and compressions (scalings) as well as shifts. The prototype wavelet can be thought of as a bandpass filter, and the constant-Q property of the other band-pass filters (wavelets) follows because they are scaled versions of the same prototype. The prototype is often called the mother wavelet. Therefore, in WT, the notion of scale is introduced as an alternative to the frequency, leading to the so-called time-scale representation. This means that the signal is mapped to a time-scale plane (the equivalent of the time-frequency plane in STFT).

The objective of feature extraction is to extract relevant information from a signal by transforming it. Some transform methods make assumptions about the signal to be analyzed. This may yield sharp results if these assumptions are valid. One such assumption is that the signal is stationary, that is, its properties do not evolve over time. For such signals x(t), the natural stationary transform is the well-known Fourier Transform. However, an abrupt change in the signal x(t) in time would spread over the whole frequency axis in X(ω)), if analyzed via Fourier transform methods. Therefore, an analysis adapted to non-stationary signals requires more than the Fourier Transform.

The usual approach is to introduce time dependency in the Fourier analysis while preserving linearity. The idea is to introduce local frequency (local in time) or instantaneous frequency parameters so that the local frequency looks at the signal through a window in time over which the signal is fairly stationary. This is the basis for the well known STFT. One drawback of the STFT is the limitations of the STFT with respect to discriminating between two pure sinusoids. Two sinusoids can only be discriminated if they are more than Δω apart in the frequency domain. Thus, the frequency resolution of STFT is given by Δω. Similarly, two pulses can only be discriminated in time if they are Δt apart. The resolution cannot be improved in both time and frequency simultaneously, because their product is bounded:

$$\Delta t \Delta \omega \geq \frac{1}{4\pi}$$

Thus, different features in the signal can be analyzed with good time resolution or frequency resolution, but not both.

To overcome the resolution limitation of STFT, the resolutions of Δt and Δω can be varied in the time-frequency plane in order to obtain multiresolution analysis. Intuitively, the time resolution of the analysis must increase (Δt must decrease) as the analysis frequency increases. Since Δt and Δm are inversely related, this implies that Δω be proportional to ω. That is:

$$\frac{\Delta \omega}{\omega} = c$$

where c is a constant. Hence the analysis has a constant bandwidth relative to the frequency. This is the essence of the well known wavelet analysis which is achieved by using a short window (compressed wavelet) for analyzing higher frequencies and a long window (dilated wavelet) for analyzing lower frequencies. The scale factor in the wavelets thus becomes analogous to the frequency of STFT, with added control over time-frequency resolution in the case of WT.

The wavelet transform is well known in the art and is not, in and of itself a novel aspect of the present invention. However, the wavelet analysis in combination with the other components of the present invention is one of the novel aspects of the present invention. Therefore, a brief discussion of the mathematical basis of the wavelet transform is given below to provide a background which will be useful in the subsequent discussion of the Fuzzy Wavelet Analysis of the present invention Let $x(t) \in E\ L^2(R)$ be the signal to be analyzed. Let a, b∈R, where a is a scaling factor and b is translation in time. A family of signals is chosen, called wavelets $\{\Psi_{a,b}\} \in L^2(R)$, for different values of a and b given by $$\Psi_{a,b}(t) = |a|^{-\frac{1}{2}} \psi\left(\frac{t-b}{a}\right) \quad \forall a, b \in R \qquad \text{Equation 14}$$

where Ψ(t) is called the mother wavelet and should satisfy the following property:

$$2\pi \int \frac{\hat{\psi}(\omega)}{|\omega|} d\omega < \infty \qquad \text{Equation 15}$$

where $\hat{\psi}(\omega)$ is the Fourier Transform of Ψ(t). Equation 15 is called the admissibility condition for the mother wavelet and is satisfied when $\hat{\psi}(0)=0$. In other words $$\int_{-\infty}^{\infty} \psi(t)dt = 0 \qquad \text{Equation 16}$$

Figure 7:
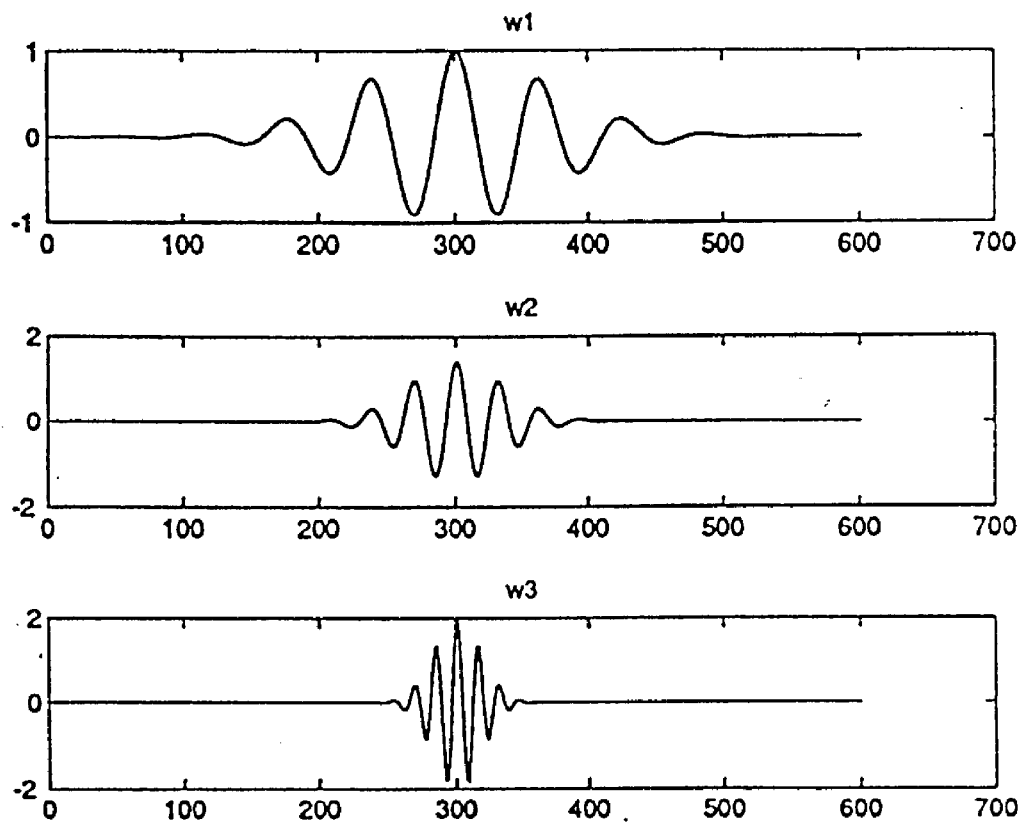
FIG. 7 illustrates an example of a wavelet having different scale factors.

Another condition on the wavelet is that its time-bandwidth product should be relatively small. This is to ensure the time/frequency localization property of the wavelet transform. Typically, a mother wavelet is a localized sinusoid. An example of a wavelet $\Psi(t)=e^{-t^2} \cos 7t$ with scale factor a=1,0.5, . . . , 0.25 is shown in FIG. 7.

The coefficients for the WT for some a and b are defined as the inner product in $L^2(R)$ of x(t) and $\Psi_{a,b}(t)$ as $$c_{a,b} = <x, \psi_{a,b}> = \int_{-\infty}^{\infty} x(t)\psi_{a,b}(t)dt \quad \text{Equation 17}$$

The signal x(t) can be recovered from its wavelet transform via the known resolution of the identity as follows $$x = \frac{1}{C'_\psi} \int_{-\infty}^{\infty} \int_{-\infty}^{\infty} \frac{c_{a,b}\psi_{a,b}}{a^2} da\,db \quad \text{Equation 18}$$

where $$C_\psi = 2\pi \int \frac{\hat{\psi}(\omega)}{|\omega|} dw \quad \text{Equation 19}$$

For the discrete case the wavelet coefficients are obtained as:

$$c_{a,b} = \sum_{j=0}^{N} x(j)\psi_{a,b}(j) \quad \text{Equation 20}$$

where N is the number of samples for which $\Psi_{a,b}(j) \neq 0$.

Now that the characteristics of the wavelet transform have been fully-discussed, the implementation of the wavelet transform in the context of the FWA of the present invention will now be discussed.

3. Fuzzy Wavelet Analysis (FWA)

The Fuzzy Wavelet Analysis of the present invention, described in detail below, capitalizes on tools such as fuzzy logic, possibility theory, multiresolution wavelet transform, time/frequency analysis and fractal scanning for providing a robust fault detection and identification scheme. The object of FWA is to use the fault features generated by the wavelet transforms to detect and identify defects. The input signal to the FDI system first undergoes preprocessing and then features are extracted using the wavelet transform. The features are fuzzified and an inference engine uses the knowledge-base to generate decisions. The fuzzification process of the present invention adapts dynamically to the external disturbances so that the performance can be improved. The detailed description of these units is given below.

a. Preprocessing

Figure 8:
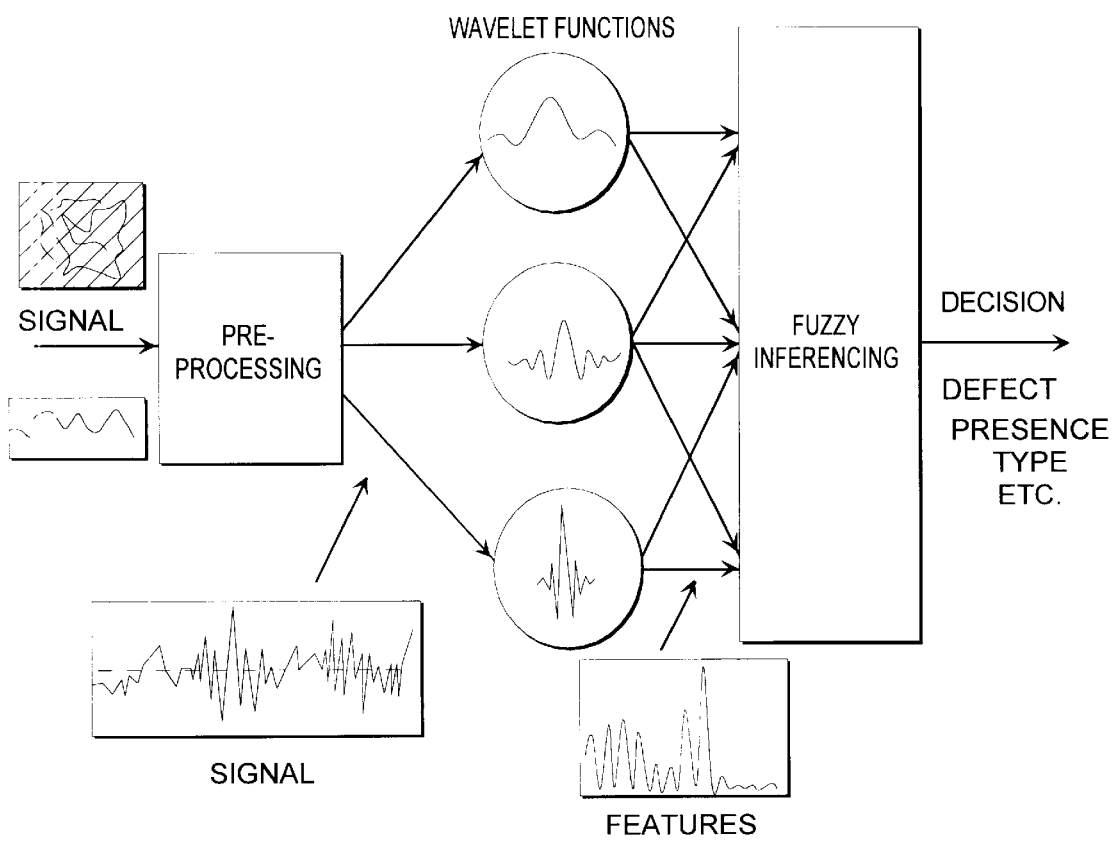
FIG. 8 is a block diagram of the Fuzzy Wavelet Analysis of the present invention.

The input signal x(t) is converted into a stream of 1-D data by the fractal scanning algorithm. This data, as shown in FIG. 8, undergoes preprocessing 10 in order to reduce the noise content and increase usability. It will be apparent to those skilled in the art that various preprocessing techniques can be applied which depend upon the particular application of the FDI system of the present invention. The preprocessing techniques may vary from simple averaging to various signal processing algorithms. However, in the case of analysis of 2-D images, the data must be converted first to 1-D data stream as mentioned above. Thus in each case (1-D or 2-D) the final signal x(t) is a 1-D data stream. The input signal x(t) is sampled at regular intervals to obtain the sampled signal x(j), j∈N. Preliminary adjustments are made at this stage to obtain a uniform mean and variance of the signal. This is helpful in suppressing external variations and sensor imperfections, and is achieved by an on-line learning system that is explained in detail below.

b. Feature Extraction

As shown in FIG. 8, FWA employs the wavelet transform (WT) using different wavelet functions 12 to extract features from the signal x(j). This is illustrated in FIG. 8. The wavelet transform generates wavelet coefficients which are combined by a fuzzy inference mechanism 15. As discussed earlier, a wavelet is represented as $\Psi_{a,b}$, where $\Psi$ is the mother wavelet, a is the scaling factor and b is the translation in time or space depending upon the context. n∈N number of wavelet scales are chosen which produce best results for the anticipated defects. The set of wavelets for some b is given by D={$\Psi_{a1,b}, \Psi_{a2,b}, \Psi_{a3,b}, \ldots, \Psi_{an,b}$}. The choice of the wavelet scales $a_i$, i=1, . . . , n, is obtained by an optimization process that works off-line. The wavelet coefficients for each wavelet $\Psi_{a,b}$ and the input signal x(j) are calculated as $$\acute{c}_{a,b} = \sum_{j=0}^{N} x(j)\psi_{a,b}(j) \quad \text{Equation 21}$$

where N is the number of samples for which $\Psi_{a,b}$ is non-zero. Since most of the faults produce a signature in a wide range of frequencies that is spread over a range of time (or space), m>0 number of coefficients $\acute{c}_{a_i}$ are buffered. A transformation $\chi$ is applied to the wavelet coefficients to get a trend of the fault signature.

$$c_{ji} = \chi(c'_{a_i,b_j}) \, i=1, \ldots, n, \, j=1, \ldots, m$$

The transformation $\chi$ varies from one application to another. It can be, for example, envelope extraction, magnitude of a complex value, etc. The transformation $\chi$ involves scaling so that $\max\{c_{ji}\} \leq 1$. The coefficients $c_{ij}$ are stacked in a matrix arrangement which is referred to as Information Matrix W, since it stores the information about all the faults.

The matrix W with elements $c_{ji}$ has the following characteristics: (1) for a fixed j=u, the $c_{ui}$'s give the frequency response of the input signal at a particular instant; (2) for a fixed i=v, the $c_{jv}$'s give the relative level of a particular frequency over a period of time (or space); and (3) each column of the matrix W is referred to as $w_i$, i=1 . . . n, and is comparable to a bandpassed version of the signal.

The matrix W is represented as follows $$\underset{\text{Time/space} \downarrow}{W} = \begin{bmatrix} c_{11} & c_{12} & c_{13} & \cdots & c_{1n} \\ c_{21} & c_{22} & c_{23} & \cdots & c_{2n} \\ \cdot & \cdot & \cdot & & \cdot \\ \cdot & \cdot & \cdot & & \cdot \\ \cdot & \cdot & \cdot & & \cdot \\ c_{m1} & c_{m2} & c_{m3} & \cdots & c_{mn} \end{bmatrix} \quad \text{Equation 22}$$

Frequency →

The columns, $\omega_i$, represent the features obtained from the input signal. $w_i \in U \subset R^m$ is the input space to the FDI algorithm of the present invention and are vague representations of the fault modes.

c. Knowledge-Base

The knowledge base of the expert system of the present invention stores the information which is helpful in decision making. It attempts to organize all the information available about the system and its faults through mathematical models, experience, heuristics, human expertise or any other source. The knowledge-base of the FWA contains the representative features for the different wavelet scales, for each one of the anticipated faults. The knowledge-base is represented by $\kappa \subset B = U \times V$ fuzz space, where $U = U_1 \times \ldots \times U_n$ is the input space and V is the output space.

The generation of the knowledge-base is done off-line. Optimized versions of $\omega_i$ are saved as $\beta_{ai,k}$ which represent the trends for scale $a_i$ (frequency) for the kth fault (k=1 . . . M), where M is the total number of anticipated faults. The optimization process chooses the best set of wavelet scales ($\alpha_i$) and stores the template features for these scales. The process of generation of κ is outlined below.

1. Experimental Analysis of Known Faults: Signal data representing faults from the system under observation are collected and stored.
2. Initial Guess of Wavelet Functions: A finite number, n, of wavelet functions are initially chosen with arbitrary wavelet scales. The choice of n is initially based on heuristics, but if the FWA system fails to perform adequately after optimization, its value can be increased.
3. Formation of the Information Matrix: The wavelet coefficients are calculated using the selected wavelet function and are stored in the information matrix. The $\omega_i$ components of the information matrix now represent the reference features and are called $\beta_{ai,k}$ (reference feature with scale $a_i$ for the kth fault).
4. Optimizing the Wavelet Scales: The components, $\beta_{ai,k}$, of the information matrix are optimized by changing the wavelet scales, $\alpha_i$, to maximize the detectability and identifiability measures.
5. Formation of the Rule-Base: The optimized $\beta_{ai,k}$ are then fuzzified into corresponding fuzzy sets $F^l_i$ (the fuzzification process is explained in detail below for the lth defect rule. Output sets Gl are constructed as fuzzy singletons as follows:

$$\{0/1+0/2+\ldots 0/(l-1)+1/l+0/(l+1)+\ldots 0/L\}$$

The lth component, $R^l$ of the fuzzy relation is constructed as follows:

$$R^l = F_1^{1*} F_2^{l*} \ldots * F_n^{l*} G^l, l=1, \ldots, L$$

where * is one of the T-norms given in Equation 23. $R^l \in U \times V$, l=1, ..., L, constitute the knowledge-base k. L is the total number of IF-THEN rules.

$$\begin{aligned}
\mu_A(x) * \mu_B(x) &= \min(\mu_A(x), \mu_B(x)) \\
\mu_A(x) * \mu_B(x) &= \mu_A(x)\mu_B(x) \\
\mu_A(x) * \mu_B(x) &= \max\{0, \mu_A(x) + \mu_B(x) - 1\} \\
\mu_A(x) * \mu_B(x) &= 1 - \min[1, ((1-\mu_A(x))^p + (1-\mu_B(x))^p)], p \geq 1
\end{aligned}$$
Equation 23 d. Fuzzification

The fuzzification unit of the FWA calculates the degree of membership of the features $\omega^i$ with the templates of the knowledge-base. The methodology presented here for formation of fuzzy sets for the elements of rule base κ is different from the conventional approach. Previous approaches are more inclined towards analysis of stream of data or similarity of possibility distributions. The approach presented here fits in the framework of fuzzy analysis to a greater extent and is especially useful in fuzzy interpretation of wavelet transforms. The FWA of the present invention preferrably uses a similarity measure given in Equation 24 for the fuzzification of the input features. However, it will be apparent to those skilled in the art that the conventional approach for formation of the fuzzy sets can be used as well.

$$sim(X,Y) = \frac{1}{K} \sum_{i=1}^{K} \frac{1-|x_i-y_i|}{1+\alpha|x_i-y_i|}$$
Equation 24

The membership function $\mu_A(x)$ is defined using the similarity function defined in Equation 24 as follows:

$$\mu_A(x) = sim(C,x)$$
Equation 25 where $C \in X$ is a crisp vector whose value is decided a priori.

Based on the definition in Equation 26, the input to the inference engine, $\overline{A}=(A_1, \ldots, A_n) \in U$, is the grade of membership of the vector $\omega_i$ in $\beta_{ai,k}$, which is given as:

$$\mu_{A_1}(\omega_i) = sim(\beta_{a_ik}, \omega_i), k=1 \ldots M$$
Equation 26

The fuzzy set $A_i$ as M elements which correspond to degree of belonging of $w_i$ in each of the fault modes.

Likewise, the fuzzy sets $F^1_i$ are obtained as the degree of memberships of defects signatures in the rule-bases with each other. For an lth defect, the fuzzy set $F^1_i$ is given as follows:

$$\mu_{F^1_1}(\beta_{a_i,k}, \beta_{a_i,l}), k=1 \ldots M$$
Equation 27 e. Fuzzy Inferencing

Inferencing or decision making is done by a set of IF-THEN rules. Let the input universe of discourse be $U=U_1 \times \ldots \times U_n$ and the output universe of discourse be V. The input (fault features) variables are $w_i \in U_i$, $w=(w_1, \ldots, w_n) \in U$, and output variable is $y \in V$. $\omega_i$ are the columns of the information matrix and output (decision) variable is $y \in V$: $F^l_i$ and $G^l$ are fuzzy sets in $U_i$ and V, respectively. The rules-set is given as follows:

Equation 28 if $w_1$ is $F_1^1$ and $w_2$ is $F_2^1$ and ... and $w_n$ is $F_n^1$ then y is $G^1$ if $w_1$ is $F_1^2$ and $w_2$ is $F_2^2$ and ... and $w_n$ is $F_n^2$ then y is $G^2$

.
.
.

f $w_1$ is $F_1^L$ and $w_2$ is $F_2^L$ and ... and $w_n$ is $F_n^L$ then y is $G^L$ Typically, one rule is sufficient for the identification of each type of defect. Hence, the number of rules is equal to the number of defects, that is, L=M.

The output fuzzy set B in V is calculated as $B=\kappa \circ \overline{A}$, where ∘ is the fuzzy composition given by Equation 29 as follows:

$$\mu_{B^1}(y) = sup_{x_i \in U}[\mu_{F^1_{1x} \ldots xF^1_n \to G^1}(\overline{x},y) * \mu_A(x)]$$
Equation 29

Since κ is composed of a number of relational rules, each rule generates an output $B^1 = R^l \circ \overline{A}$. The first step in achieving this is to calculate the premise part, that is, $\hat{A}: A_1$ and $A_2$ and ... and $A_n$ This is done mathematically as follows:

$$\hat{A} = A_1 * A_2 * \ldots * A_n$$
Equation 30 where * is one of the T-norms given in Equation 23. The next step is to compare $\hat{A}$ with the rulebase and generate the output fuzzy set $B^l$, $$\mu_{B^l}(y) = sup_{w \in U}[\mu_{R^l}(\omega,\gamma) * \mu_{\hat{A}}(\omega)]$$

The final output is obtained by applying one of the S-norms given in Equation 31 in Equation 32 as follows:

$$\mu_A(x) \dot{+} \mu_B(x) = \max(\mu_A(x), \mu_B(x)) \quad \text{Equation 31}$$
$$\mu_A(x) \dot{+} \mu_B(x) = \mu_A(x) + \mu_B(x) - \mu_A(x)\mu_B(x)$$
$$\mu_A(x) \dot{+} \mu_B(x) = \min\{1, \mu_A(x) + \mu_B(x)\}$$
$$\mu_A(x) \dot{+} \mu_B(x) = \min[1,((\mu_A(x))^p + (\mu_B(x))^p)], p \geq 1$$

$$\mu_{B^l}(y) = \mu_B(y) \dot{+} \mu_B(y) \dot{+} \ldots \dot{+} \mu_B(y) \quad \text{Equation 32}$$

The fault mode is identified by defuzzifying the final output fuzzy set B:

$$y = \arg\sup\nolimits_y \in \nu(\mu_B{}^l(\gamma)) \quad \text{Equation 33}$$

The output of Equation 33 gives the decision that the yth defect has occurred.

f. Performance Metrics

Once a decision about the defect has been reached, the FWA assigns a Degree of Certainty (DOC) to the fault decision. DOC is a measure of confidence in the decision. It is used to take-into account the uncertainty inherent in the system. Under perfect recall conditions the output of the inference engine, $B^l$, would be identical to the output association, $G^l$, in the training set. However, under normal operating conditions $B^l$ and $G^l$ do not match perfectly due to a large grain uncertainty in the input. DOC gives an indication of the closeness of the actual decision to the original training output.

$$DOC_l = h(G^l B^l), l = 1, 2, \ldots, L \quad \text{Equation 34}$$

where, $h: [0,1] \to [0,1]$ $$h = \frac{\mu_{B^l}(y^l)}{\mu_{G^l}(y^l)} \quad \text{Equation 35}$$

Since, in this case $G^l$ is defined as a singleton, $$DOC_l = \mu_{B^l}(\gamma^l) \quad \text{Equation 36}$$

A value of $DOC_l = 1$ indicates a perfect recall for the lth rule, while on the other hand a value of $DOC_l$ close to 0 implies that the belief of the occurrence of that particular feature is very small. The values of DOC indicate the robustness of the decision making logic of the inference mechanism.

g. Detectability and Identifiability Measures

Identifiability and detectability are measures of robustness of the FDI scheme which aims at minimizing the sensitivity of detection performance of modeling errors, uncertainties and system noise. Detectability is the extent to which the FDI scheme can detect the presence of faults. It relates to the smallest fault signature that can be detected and the percentage of false alarms. Identifiability of the FDI system goes one step further in distinguishing between various fault modes once the presence of a fault has been established. Identifiability targets questions like the source, location, type and consequence of failure and the distinguishability between sensor, actuator or system failures.

In intelligent schemes, detectability and identifiability depend upon a number of factors that may vary from one system to another. For the EWA analysis introduced here, the detectability $D_k(a_i)$ of the kth fault from a stream of signal data x(t) is given by $$D_k(\alpha_i) = 1 - e^{-d_k(\alpha_i)} i = 1, \ldots n \quad \text{Equation 37}$$

where $$d_k(a_i) = \max_{a_1, \ldots, a_n} \left\{ \frac{F_k(a_i)}{N(a_i)s} (1 - \lambda|L_{\psi a_1} - L_k|) \right\} i = 1, \ldots, n \quad \text{Equation 38}$$

and $F_k(\alpha_i)$ = magnitude of the feature in $w_i$ for the scale $a_i$ for the kth fault, $N(\alpha_i)$ = mean square value of the random noise in $w_i$ for the scale $a_i$, $L_{\psi_\alpha}$ = length of the wavelet function for the scale $a_i$, S = factor for decimation, e.g., scale factor in fractal scanning, $L_k$ = length of feature for the kth fault, $\lambda$ = constant less than 1

The logic behind using the maximum value for the detectability is that even if a single wavelet frequency is triggered, it is sufficient for detecting the presence of the fault. This however is not the case in identifiability where more information is also required.

The greater the value of $D_k$, the greater the detectability of the kth fault. The identifiability, $I_k$, of a particular fault k depends on how clearly it relates to the rule-base and how different it is from other faults. If $w_{i,k}$ is the feature for the kth fault using $a_i$th scale, a measure of $I_k$ is given below $$I_k(a_i) = \frac{1}{n} \left( \sum_{i=1}^{n} sim(w_{i,k}, \beta_{a_i,k}) - \sum_{i=1}^{n} \sum_{p=1, p \neq k}^{M} sim(w_{i,p}, \beta_{a_i,k}) \right) \quad \text{Equation 39}$$

$$i = 1, \ldots, n$$

It can be observed that detectability and identifiability measures entail different levels of intelligence of the knowledge hierarchy. Detectability belongs in the information level as it contains a notion of signal to noise ratio (data) along with the window parameters (limited time horizon). On the other hand, identifiability can be classified into the Knowledge level as it uses the whole knowledge-base in a vast horizon.

4. Learning

An important attribute of intelligent systems is their ability to restructure or update the knowledge-base, based on information from past experience. This is termed as learning. The FWA of the present invention preferably uses both on-line and off-line learning to increase the knowledge of the system and to thereby improve the detection and identification processes.

a. On-Line Learning

There are a number of factors that produce unanticipated noise variations in the input signal. As an example, noise variations are often encountered in the digital images of CCD cameras. These noise variations are low frequency variations resulting mainly from the following factors: (1) variation in lighting and illumination; (2) imperfections of the CCD sensor element; and (3) spherical aberration of the lens.

The goal of on-line learning or adaptability is to nullify the effects of the above-mentioned factors by adjusting the FWA parameters in the opposite direction. This is utilized at two stages: (1) during preprocessing of the input signal; and (2) at the time of fuzzification.

At the preprocessing stage, the system of the present invention is designed to obtain information from the statistical evidence contained in the input signal x(n) through a finite memory model. The mean of the signal $x_{DC}$ is calculated by moving average estimator:

$$x_{DC}(n) = \frac{1}{N+1} \sum_{i=0}^{N} x(n-i) \qquad \text{Equation 40}$$

The variance of the signal $\sigma_x$ is calculated by:

$$\sigma_x(n) = \frac{1}{N+1} \sum_{i=0}^{N} (x(n-i) - x_{DC}(n))^2 \qquad \text{Equation 41}$$

The input signal is scaled by a factor K(n):

$$x(n) = K(n) x'(n) \qquad \text{Equation 42}$$

The value of K is updated as:

$$K(n) = K(n-1) + L_1(\sigma_{normal} - \sigma_x(n)) \qquad \text{Equation 43}$$

Where $\sigma_{normal}$ is the required variance in the signal, and $L_1$ is the learning coefficient (typically 0.01). The learning coefficient attempts to minimize deviations in the variance of the input signal.

At the fuzzification stage, the system of the present invention uses the similarity function to maintain a predetermined level of fuzziness (entropy) of the inference engine. The value of $\alpha$ in the similarity relation is adjusted so that the fuzzy membership value of the sets $\omega_i$ given by $\mu_{A_i}(\omega_i)$ is close to $\mu_N$, a constant defined a priori (typically 0.2). The value of $\alpha$ for the sample n and the scale $\alpha_i$ is updated by:

$$\alpha_i(n) = \alpha_i(n-1) + L_2(\mu_N - \mu_{A_i}(\omega_i)) \qquad \text{Equation 44}$$

$L_2$ is the learning coefficient (typically 0.01).

b. Off-Line Learning

The off-line learning process of the present invention provides the FWA with the ability to generate its knowledge-base from sample defects. This is an optimization process which selects the optimum wavelet scales for the given set of defects and stores the corresponding features in the rulebase.

As discussed above, the wavelet coefficients act as frequency discriminators on a localized time basis. Different fault features respond differently to various frequencies. Hence it is important to choose a set of wavelet functions that span the frequency range of all the anticipated defects. It is also required that the wavelets in this set are tuned to different fault features. This implies that the wavelet coefficients generated by one defect would be quite distinct from coefficients of other defects, hence increasing the identifiability of the system.

The process of tuning the wavelet scales is accomplished off-line through an optimization process. The goal is to maximize the minimum detectability $D_k$, $k=1, \ldots, M$, and the combined identifiability $I_k$, while keeping the detectability and identifiability of the other defects above a predetermined threshold. This can be written as $$J(a_i) = \max_{a_1, \ldots, a_n} \left\{ \left( \min_k \{D_k(a_i)\} \right) + \left( \sum_{k=1}^{M} I_k(a_i) \right) \right\}, \quad i = 1, \ldots, n \qquad \text{Equation 45}$$

subject to $$D_k > T_{Dk} = 1, \ldots M.$$

$$I_k > T_{Ik} = 1, \ldots M.$$

$T_D$ and $T_I$ are the minimum acceptable levels of detectability and identifiability, respectively, for any defect. The scales $a_i$ are varied within predetermined ranges, so that the value of J is maximized.

Since there is no input signal (only reference signals are used) in this case and only the members of the rule-base are to be compared, $D_k(\alpha_i)$ and $I_k(\alpha_i)$, as given in Equation 37 and 39, become:

$$D_k(\alpha_i) = 1 - e^{-d_k(\alpha_i)} i = 1, \ldots, n \qquad \text{Equation 46}$$

and $$d_k(a_i) = \max_{a_1, \ldots, a_n} \left\{ I_k(a_i) \frac{F_k(a_i)}{N(a_i)s} \left(1 - \lambda |L_{\psi a_i} - L_k| \right) \right\} \quad i = 1, \ldots, n \qquad \text{Equation 47}$$

where $F_k(\alpha_i)$ = magnitude of the feature in the $\beta_{ai,k}$ for the scale $\alpha_i$ for the kth fault, $N(\alpha_i)$ = mean square value of random noise $\beta_{a,k}$ for the scale $\alpha_i$, $L_{\psi a_i}$ = length of the wavelet function for the scale $a_i$, s = factor for decimation, e.g., scale factor in fractal scanning, $L_k$ = length of feature for the kth fault, $\lambda$ = constant less than 1

$$I_k(a_i) = \frac{1}{n} \left( \sum_{i=1}^{n} sim(\beta_{a_i,k}, \beta_{a_i,k}) - \sum_{i=1}^{n} \sum_{p=1, p \neq k}^{M} sim(\beta_{a_i,p}, \beta_{a_i,k}) \right) \quad i = 1, \ldots, n \qquad \text{Equation 48}$$

Since $sim(\beta_{a_i}i, \beta_{a_i k}) = 1$ $$I_k(a_i) = \frac{1}{n} \left( \sum_{i=1}^{n} 1 - \sum_{i=1}^{n} \sum_{p=1, p \neq k}^{M} sim(\beta_{a_i,p}, \beta_{a_i,k}) \right) \quad i = 1, \ldots, n \qquad \text{Equation 49}$$

or $$I_k(a_i) = \frac{1}{n} \left( n - \sum_{i=1}^{n} \sum_{p=1, p \neq k}^{M} sim(\beta_{a_i,p}, \beta_{a_i,k}) \right) \quad i = 1, \ldots, n \qquad \text{Equation 50}$$

Identifiability requires that the similarity of the input features be as close as possible to the template of the corresponding defect in the knowledge-base, yet very different from the templates of all other defects. This means that the similarity measure between the input feature and its corresponding template be close to 1 and near 0 for the others. If this is not the case, then the similarity measures will be in the interval (0,1), and the certainty of association to one category and disassociation to other categories decrease. This is similar to the notion of entropy. Entropy, being a measure of fuzziness, is high when the values of the fuzzy set are around 0.5. If the values are close to 1 or 0, the set is more crisp and its entropy is low. Hence, if the identifiability of the system is high, the entropy of the knowledge-base is low and has less uncertainty. Therefore, an intuitive link between identifiability and system entropy is established.

Apart from the intuitive link, a mathematical link between fuzzy entropy and identifiability can also be established. Consider the most general form of entropy as given in Equation 51. Since there are finite number of elements in the knowledge-base, the integral sign in Equation 51 changes to summation. The entropy of the kth rule of the knowledge-base B, is given as follows:

$$H_k(B) = \frac{1}{n} \sum_{i=1}^{n} \sum_{p=1}^{M} f(\mu_{A_{i,p}}(w_{i,k}))  \quad \text{Equation 51}$$

$$e(A) = \int_X f(\mu_A(x))dv \quad x \in X \quad \text{Equation 52}$$

where f is any function f:[0,1]→[0,1], such that f is monotonically increasing in the [0,½] interval and monotonically decreasing in the [½,1] interval, as given in Equation 52.

According to Equation 26, $\mu_{A_{i,p}}(\omega_{i,k})=\text{sim}(\beta_{a_{i,p}}, A_{i,k})$, p=1, ..., M. Hence, $$H(B) = \frac{1}{n} \sum_{i=1}^{n} \sum_{p=1}^{M} f(sim(\beta_{a_{i,p}}, w_{i,k})) \quad \text{Equation 53}$$

or $$H(B) = \frac{1}{n} \sum_{i=1}^{n} \left( f(sim(\beta_{a_{i,p}}, w_{i,k})) + \sum_{p=1, p\neq k}^{M} f(sim(\beta_{a_{i,p}}, w_{i,k})) \right) \quad \text{Equation 54}$$

Let f be a triangular function given by:

$$f(x) = \begin{cases} x & \text{for } x \in [0, 1/2] \\ 1-x & \text{for } x \in [1/2, 1] \end{cases} \quad \text{Equation 55}$$

For most practical cases $$sim(\beta_{a_{i,p}}, w_{i,k}) \begin{cases} \geq 1/2 & \text{for } p = k \\ \leq 1/2 & \text{for } p \neq k \end{cases} \quad \text{Equation 56}$$

Hence, we can replace $(f(\text{sim}(\beta_{a_{i,k}}, \omega_{i,k}))$ by $1-\text{sim}(\beta_{a_{i,k}}, \omega_{i,k})$ and f $(\text{sim}(_{a_{i,p}}, \omega_{i,k}))$ by sim $(\beta_{a_{i,p}}, \omega_{i,k})$ $$H_k(B) = \frac{1}{n} \sum_{i=1}^{n} \left( 1 - sim(\beta_{a_{i,k}}, w_{i,k}) + \sum_{p=1, p\neq k}^{M} sim(\beta_{a_{i,p}}, w_{i,k}) \right) \quad \text{Equation 57}$$

or $$H_k(B) = 1 - \frac{1}{n} \left( \sum_{i=1}^{n} sim(\beta_{a_{i,k}}, w_{i,k}) - \sum_{i=1}^{n} \sum_{p=1, p\neq k}^{M} sim(\beta_{a_{i,p}}, w_{i,k}) \right) \quad \text{Equation 58}$$

Using Equation 39:

$$H_k(B) = 1 - I_k \quad \text{Equation 59}$$

Since $I_k \in [0,1]$, it can be seen from Equation 59 that maximizing identifiability means minimizing the entropy of the system and vice versa. In other words, $H = \bar{I}$, that is, entropy is the complement of the identifiability, as predicted intuitively.

c. Off-Line Learning Using a Genetic Algorithm

In accordance with the preferred embodiment of the present invention the optimization problem given in Equation 46 is solved by using a known Genetic Algorithm (GA). Alternatively, other methods, such as calculus-based methods, can be used to solve the optimization problem. GAs are search algorithms based on the mechanics of natural selection and genetics. They combine survival of the fittest among string structures with a structured, yet randomized, information to form a search algorithm.

Genetic Algorithms were developed by John Holland and his colleagues at the University of Michigan. The goals of their research have been two-fold:

1. To abstract and rigorously explain the adaptive processes of natural systems; and 2. To design artificial software that retains the important mechanism of natural systems.

Figure 9A:
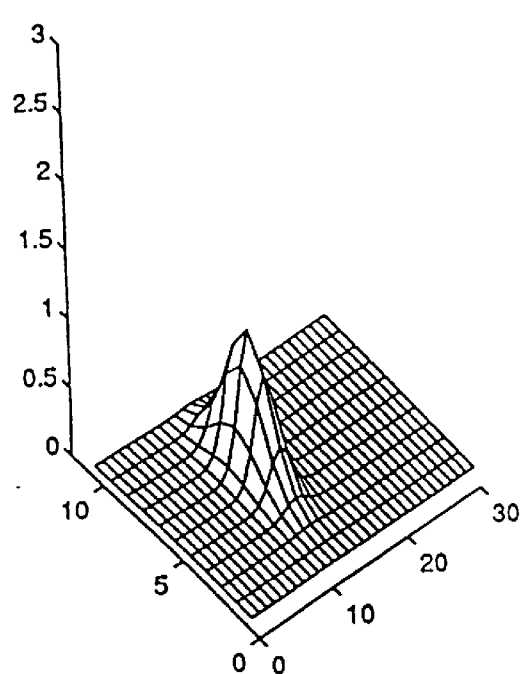
FIGS. 9a and 9b illustrate problems with using calculus-based methods to select optimum wavelet scales.
Figure 9B:
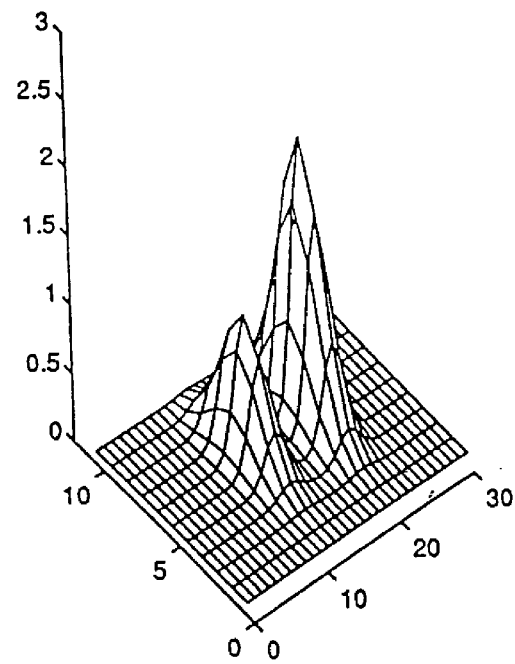
Figure 10:
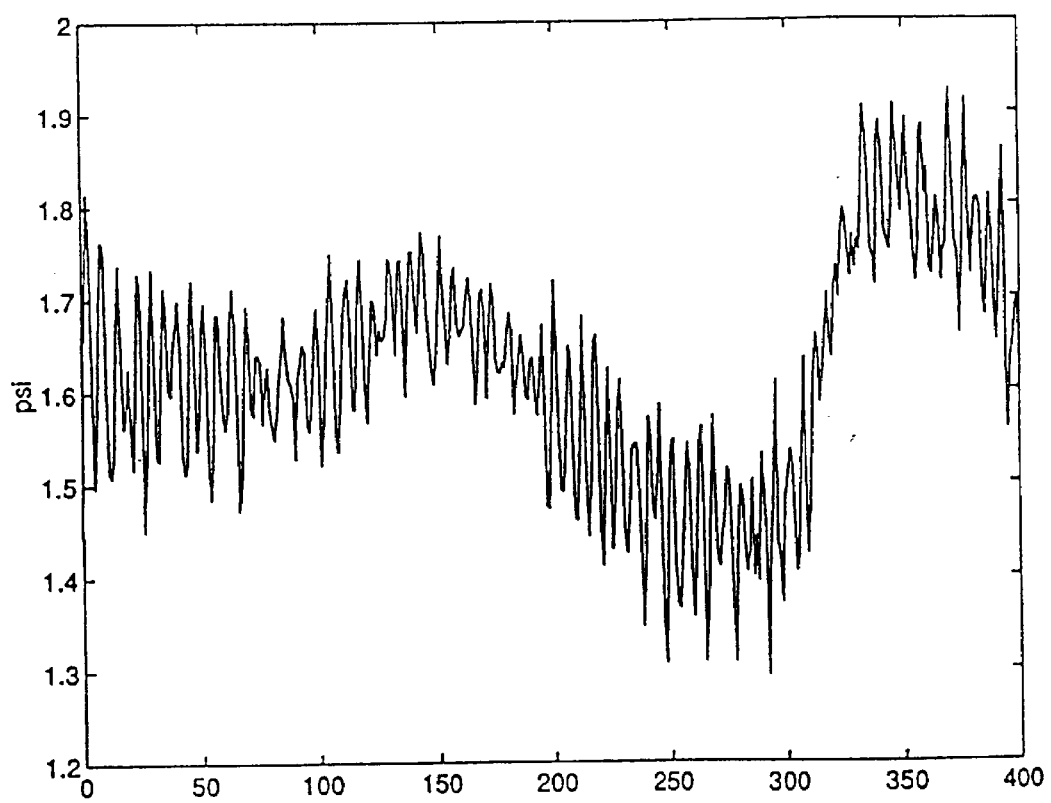
FIG. 10 illustrates a noisy signal for which calculus-based methods would be unsuitable for selecting optimum wavelet scales.

In comparing GAs with calculus-based methods, it is apparent that there are distinct advantages and disadvantages to both. Calculus-based methods of optimization have been studied extensively. These are subdivided into two main classes: indirect and direct methods. Indirect methods seek local extrema by solving the usually nonlinear set of equations resulting from setting the gradient of the objective function equal to zero. This is a multidimensional generalization of the elementary callous notion of extreme points, as illustrated in FIG. 9a. Given a smooth, unconstrained function, finding a possible peak starts by restricting the search to those points with slopes of zero in all directions. On the other hand, direct (search) methods seek local optima by hopping along the function in the direction of the gradient. This is simply a notion of hill climbing: to find the local best, climb the function in the steepest permissible direction. Both of these methods are local in scope; the optima they seek are best in a neighborhood of the current point. In case of a function as in FIG. 9b, starting the search in the neighborhood of the lower peak will result in missing the main event (the higher peak). Once the lower peak is reached, further improvement is not possible. Another problem with calculus-based methods is that they are based on the existence of derivatives. In many applications the derivative of the function might not exist. As shown in FIG. 10, signals in real life are noisy and unsuitable for these traditional methods.

Due to the shortcomings of calculus-based techniques, random search algorithms have achieved increasing popularity. GAs are global in nature and the possibility of converging to a local minima is very small. They provide a robust random yet systematic search technique that is suitable for optimizing the rule-base of the FWA. The drawback of GAs is that they are computationally intensive and although their convergence is highly probable, is not guaranteed.

The GA attempts to emulate the phenomena of natural selection and reproduction based on the principle of the survival of the fittest. Some of the terms used in GAs are explained below:

Population: A set of members (variables) that are present at one time in the process of evolution.

Chromosome: A string (set of bits) that characterizes a member of population distinct from another.

Evolution: The development in the chromosomes of the population over a period of time.

Generation: A population at a particular stage of evolution.

Mating (Reproduction): The combination of chromosomes of one generation to produce offsprings of the next generation which have genetic (related to the chromosomes) traits of the parents.

Crossover: The swapping of a part (or parts) of the chromosomes of the mating members while producing chromosomes of the next generation.

Mutation: Inversion of one or more bits of the chromosomes of the mating members while producing chromosomes of the next generation.

Crossover Rate: The probability by which the crossover occurs.

Mutation Rate: The probability by which the mutation occurs.

Elitism: Since the best chromosomes might be destroyed due to mutation and crossover, one way of avoiding this is to use elitism, in which the best chromosomes in the parent population are copied into the next generation.

Steady State Reproduction: This is a further extension of elitism. In this method only a subset of the whole population is allowed to reproduce. The offsprings replace equal numbers of members that have the lowest fitness level.

Working of Genetic Algorithm:

The usual flow of a typical GA is as follows:

1. Initialize a population of chromosomes, call this number P;
2. Evaluate each chromosome in the population;
3. Create new chromosomes by mating current chromosomes; apply mutation and crossover as the parent chromosomes mate;
4. Delete members of the population to make room for new chromosomes;
5. Evaluate the new chromosomes and insert them in the population; and
6. If time is up, stop and return the best chromosomes if not, go to 3.

Mathematical Implementation of Genetic Algorithm

The free variable of the genetic algorithm is translated into a string of bits through a bijective mapping. The most convenient mapping is the binary representation of the free variable. For example, if the function $f(x)=x^2$ is to be maximized in the interval [0,3.1], one mapping X for a five bit string would be as follows:

$$x \xrightarrow{\pi} (10x)_2$$

where subscript 2 represents the binary base 2. Hence, for example, x=0.5 is represented as $(00101)_2$ and x=1.5 is represented as $(01111)_2$.

The fitness level of a member of the population is calculated by the value of the objective function given from the particular string of chromosomes for that member. The closer the value of the objective function to the required value, the more fit are the chromosomes of that member. For example, in the above mentioned case, if the objective function is $$J(x) = \max_x \{x^2\} \qquad \text{Equation 60}$$

then $(01111)_2$ is more fit than $(00101)_2$. This is because $(00101)_2$ represents x=0.5 and $(01111)_2$ represents x=1.5 and the value of the objective function is greater for x=1.5 than for x=0.5.

The process of selection of parents for reproduction is based on the underlying idea that the fittest parents should be able to mate yet the process is randomized to allow globalization of the search process. The parents are selected at random but the probability of choosing the best parents is more than that of the others. This is done by making the probability of selection of any member of the population for reproduction equal to its relative fitness level. One way of achieving this is by the so called Roulette Wheel Parent Selection, explained below:

1. Sum the fitness of all the population members; call the result the total fitness;
2. Generate r, a random number between 0 and the total fitness; and
3. Return the first population member whose fitness, added to the fitness of the preceding population members, is greater than or equal to p.

An example of roulette wheel parent selection is shown in FIG. 11. Ten chromosomes with their individual fitness and running total are shown. The second table shows the chromosomes that would be selected based on the random numbers.

The process of reproduction involves the combination of chromosome bit strings of the parents into chromosomes of children by bit crossover and mutation.

Bit Mutation: When bit mutation is applied, the bits in the chromosome string are inverted with a probability factor called mutation rate. This value is usually very low (typically 0.008).

One-Point Crossover: For one-point crossover, a crossover point is randomly selected. All the bits after the crossover point, in the parents' strings, are swapped to obtain the chromosomes of the children. The crossover rate is usually high (around 0.65).

Two-point crossover: Two-point crossover is similar to one-point crossover, except that two crossover points are randomly selected and all the bits between them are swapped. Examples of two-point crossover are shown in FIG. 12.

Implementation of GA for FWA

In accordance with a preferred embodiment of the present invention, the optimization program uses GA for off-line learning and has been implemented using MATLAB™ produced by Mathworks, Inc. of Natlick, Mass. The default value for the number of wavelet functions n is 5. However, this value can be increased if the optimization process fails to converge for the given thresholds $T_D$ and $T_I$. The initial population of P=100 members is chosen randomly. Each member is represented by a pair <S,F>, where $S=(\alpha_1, \alpha_2, \ldots \alpha_n)$ is the set of the wavelet scale and F is the fitness level of the set (value of the objective function). For the sake of clarity S and F are represented as:

$$S: S^j j=1, \ldots, P \qquad \text{Equation 61}$$

$$F: F(S^j) \qquad \text{Equation 62}$$

$a^j_i$ represents the scale $a_i$th member of the jth set. F is calculated as follows:

$$F(S_j) = D(a^j_i) = I(a^j_i) \qquad \text{Equation 63}$$

where $$D(a^j_i) = \left( \min_k \{D_k{}^j(a_i)\} \right) \qquad \text{Equation 64}$$

$$I(a^j_i) = \left( \sum_{k=1}^{M} I_k{}^j(a_i) \right)$$

where $D^j_k(\alpha_i)$ and $I^j_k(\alpha_i)$ are the detectability and identifiability measures as given in Equations 46 and 50, for the jth member of the population.

The GA used for the optimization process of the FWA uses two-point crossover with a crossover rate of 0.65 and mutation rate of 0.008.

The representative signals for the known defects are collected and stored. $n_p$ number of initial population of P members are selected at random. For a given fault k, intermediate values of detectability $d^j_{k,\alpha_i}$ are calculated for a particular j as follows:

$$d^j_{k,a_i} = \frac{F_k(a_i^j)}{N(a_i^j)s} \; (1 - \lambda|L_\psi a_i - L_k|) \quad i = 1, \ldots, n \qquad \text{Equation 65}$$

The detectability is obtained by taking the maximum value over different scales. This is equivalent to taking a maximum offer a row in the table shown in FIG. 13.

$$D_k^j = \max_{a_1^j, \ldots, a_n^j} \{1 - e^{-d^j_{k,a_i}}\} \qquad \text{Equation 66}$$

Likewise, for given k similarity measure $s^j_{k,a_i}$ of the scale, $\alpha_i$, are calculated by:

$$s^j_{k,a_i} = \sum_{p=1, p \neq k}^{M} sim(\beta_{a_i^j,p}, \beta_{a_i^j,k}) \qquad \text{Equation 67}$$

$I^j_k$ is calculated for each row in FIG. 13.

$$I_k^j = \frac{1}{n} \left( n - \sum_{i=1}^{n} s^j_{k,i} \right) \qquad \text{Equation 68}$$

Finally, $I^j_k$ and $D^j_k$ are added to get the fitness level for each member.

As shown in FIG. 13, P number of fitness levels are obtained which are associated with each set of wavelet scales. The wavelet sets are assigned as probability for reproduction according to the roulette wheel method described above. Mutation and crossover are applied to the corresponding elements of the wavelet sets. Members of the old set are deleted and replaced by the new generation. Preferably, the process is repeated until the optimization converges or for 100,000 cycles, whichever is achieved first.

5. Preferred Embodiment

The FDI system of the present invention will now be discussed in accordance with the preferred embodiment wherein it is incorporated into a textile fabric manufacturing process. The textile industry is driven by the need for quality control and monitoring in all phases of production. One very important step in quality assurance is the detection and identification of defects occurring in woven fabrics. Unfortunately, there is currently no satisfactory on-line fault detection system available and inspections usually are done manually, which is both ineffective and expensive. The FWA of the present invention has been successfully applied to defect detection and identification of textile fabrics. The system of the present invention preferably is implemented directly on the loom so that time delay between production and control is minimized.

Figure 14:
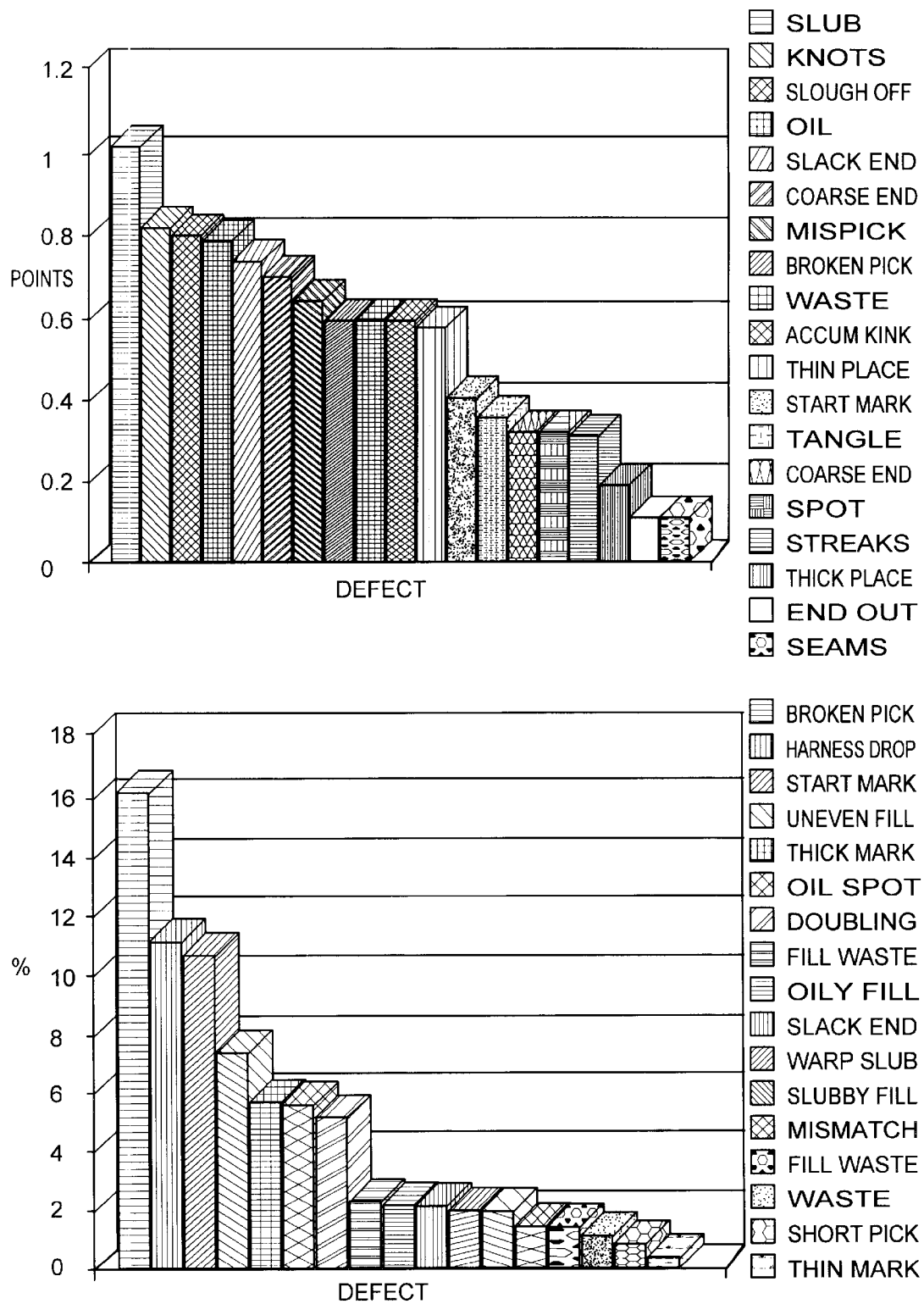
FIG. 14 lists particular types of defects which commonly occur during the manufacture of textiles.

In order to classify and prioritize textile defects, a survey was conducted by collecting data from five major textile fabric producers in Georgia and South Carolina. The defects were rated based on the most common and the most costly defects. The results of this survey are shown in FIG. 14.

A description of these defects is given below:

Abrasion: sections of fabric that appear abraded.

Blown Pick: broken pick for an air jet loom.

Bow: where filling yarns lie in an arc across the width of the fabric.

Broken End: where a warp yarn has often ruptured and been repaired; often produced by some mechanical means like chafing; often characterized by the broken end being woven into the fabric.

Broken Pick: where a filling break leaves a pick missing for a portion of the width of the fabric; often caused by weak yarn; often serious enough to cause degrading of woven fabrics.

Coarse End: an end whose diameter is noticeably greater than what is normal to the fabric.

Coarse Pick: a pick of filling whose diameter is noticeably larger than what is normal to the fabric.

Coarse Yarn: a yarn whose diameter is noticeably larger than what is normal to the fabric (may be warp or filling yarn).

Cockled Yarn: a yarn in which some fibers appear wild or tightly curled and disoriented. This is the result of some fibers being too long for the draft roll settings so that the succeeding roll grips the fiber before the preceding roll releases it, causing the fiber to snap and curl. Often appears as tiny slubs in the fabric.

Double End: two ends where only one is called for by the design of the fabric.

Double Pick: two picks in a single shed where only one is called for in the design of the fabric.

Doubling: a filling yarn twice the normal size due to two ends of a roving running together into a single end of spinning. The same occurrence in warp yarn would result in a course end. Two warps weave as one due to faulty drawing in when warp was drawn through harness prior to weaving or due to improper harness action.

End Out: a missing warp yarn; can be due to lack of strength or to breaking.

Filling Band: a visually perceptible band across the width of the fabric directly attributed to a difference in the chemical or physical characteristic of the filling.

Filling Waste: small bunches of waste of whatever was added to the filling yarns to help provide proper tension to yarns.

Flat(Reed Misdraw/Wrong Draw: a misdraw in a plain weave resulting in two ends weaving as one and opposing two other ends weaving as one.

Float: a thread extending unbound over or under threads of the opposite yarn system with which it should have been interlaced.

Fuzz Balls/Lint Balls: balls of fiber encircling the warp yarn formed by the abrasion of the loom. These usually result from the lack of sufficient sizing material on the warp yarns, causing what is generally referred to as soft warp.

Gout: an accumulation of short fiber or fly spun into the yarn or drawn into the loom shed. This defect differs from slubs in that slubs generally are symmetrical in shape while gout appears as undrafted lumps.

Hang Thread: a thread left hanging on the face of the fabric. The most common cause is the failure of a weaver to clip the excess yarn after repairing a broken end and the cloth inspector's failure to remove excess yarn.

Hard Size: a place in a fabric characterized by a harsh, stiff hand and a cloudy, uneven appearance. This is most common in mill finished yarn dyes and is the result of a slasher stop that allows excessive amounts of sizing material to harden onto the yarn. This generally appears in bands across the width of the fabric. Also caused by differences in tension or slight variations of original yarns.

Harness Balk/Harness Skip: an isolated failure of a loom harness to move in its prescribed sequence, causing a filling to float over certain warp ends with which it should have interlaced.

Harness Drop/Harness Breakdown: a place where a harness ceases to function resulting in the ends drawn through that harness floating on the face or on the back of the fabric. Also can give a dotted line appearance from the inner edges of the selvage.

Harness Misdraw: where one or more ends are drawn through the harness contrary to the design of the weave.

Kinky Filling: a place in the fabric where a pick of filling has been given enough slack to twist on itself for a short distance caused by a malfunctioning filling fork, excessive twist in the yarn, inadequate setting of filling twist.

Knot: a place where two ends of yarn have been tied together.

Loom Waste: a place in the fabric where accumulated waste off the loom has found its way into the fabric perhaps by air current.

Loop in Shed: loopy filing, a filling hanging for an instant of time on a warp knot or other protrusion until freed by the stroke of the reed. This results in a short loop of filling appearing on the face of the fabric or kinky filling, a place in a fabric where a filling has been given enough slack to twist on itself for a short distance. Probable causes are a malfunctioning of filling fork, too much power in the picking motion, excessive twist in yarn, inadequate setting of filling twist.

Loopy Filling/Hang Pick: a pick of filling hanging for a split second on a warp knot or other protrusion until freed by the stroke of the reed. This results in a short loop of filling appearing on the face of the fabric.

Mat-up: a place where the warp yarns have become entangled so as to disrupt the proper interlacing of warp and filling caused by loom failing to stop when an end breaks or the introduction of a piece of wild yarns; can be severe.

Mismatch/Mispick: where the weave design is broken by the absence of a pick or a filling.

Mixed Yarn: yarn that is alien to a fabric because of its peculiar chemical or physical characteristics, can be caused by variation in blend or twist.

Neppiness: an excessive amount of tangled mass of fiber appearing on the face of the fabric.

Oily End: a warp yarn that has been soiled by grease or dirt.

Oily Filling: filling yarn that has been soiled by grease and dirt.

Oily Spots: a discolored place or stain on a fabric, resulting from any number of sources.

Reed Mark: a defect resulting from a bent reed wire, characterized by a fine line thin place in the warp direction.

Reedy: a condition characterized by open streaks following the pattern of the reed wires. This can be the result of too coarse reed, wrong reed draw arrangement or improper setting of the loom.

Short Pick: this is the result of the filling insertion mechanism on a shuttleless loom not holding and releasing the filling yarn too soon. This allows the yarn to snap into the body, leaving a missing pick part-way across the width of the fabric. The released pick is then woven into the fabric in a somewhat tangled mass.

Skew: where the filling yarns are off square to the warp ends.

Slack End: the result of a loose or broken end puckering as it is gradually woven into the fabric.

Slack Warp: fabric woven with less than the required tension. Extremes result in an overall crimped or cockled appearance and a stretchy unstable fabric.

Slasher Oil: Like oily spot, but caused by slasher oil.

Sloughed Filling: a defect caused by extra winds of filling slipping from the bobbin and being woven into the fabric. This is usually the result of soft bobbins wound with insufficient tension or too much power on the picker stick of the loom.

Slubby Filling: a bobbin of filling containing numerous slubs (a term used to describe a short thick place in a yarn).

Slub: a term used to describe a short thick place in a yarn that is usually symmetric.

Start Mark: a mark resulting from the warp yarn elongating under tension while a loom is stopped; when the loom is restarted, the slackness is taken up by the weave, leaving a distortion across the width of the fabric.

Stop Mark: a defect resulting from the warp yarn elongating under tension while a loom is stopped; when it is started again, the slackness is taken up by the weave, leaving the distortion across the width of the fabric.

Temple Bruise: a streak along the edge of the fabric that has been scuffed and distorted by a damaged malfunctioning or poorly set temple.

Thick Place: a place across the width containing more picks or heavier filling than that normal to the fabric.

Thin Place: a place across the width containing less picks or lighter filling than that normal to the fabric.

Tight End: an end running taut due to some abnormal restriction. It tends to force the filling to the surface of the fabric and is characterized by a fine line streak of filling showing through like a reed mark.

Uneven Fabric Width: inconsistent fabric width.

Uneven Filling: a filling whose variation of diameter is noticeable enough to detract from the appearance of a fabric caused by choke on a drafting roll, poor distribution of fiber length, less than optimum draft distribution, incorrect roll settings, eccentric behavior of drafting rolls.

Wavy Cloth: cloth woven under conditions of varying tensions, preventing the even placement of filling picks resulting in a fabric with randomly alternating thick and thin places which is generally traceable to a faulty take up motion or let off motion in the loom.

Figure 15:
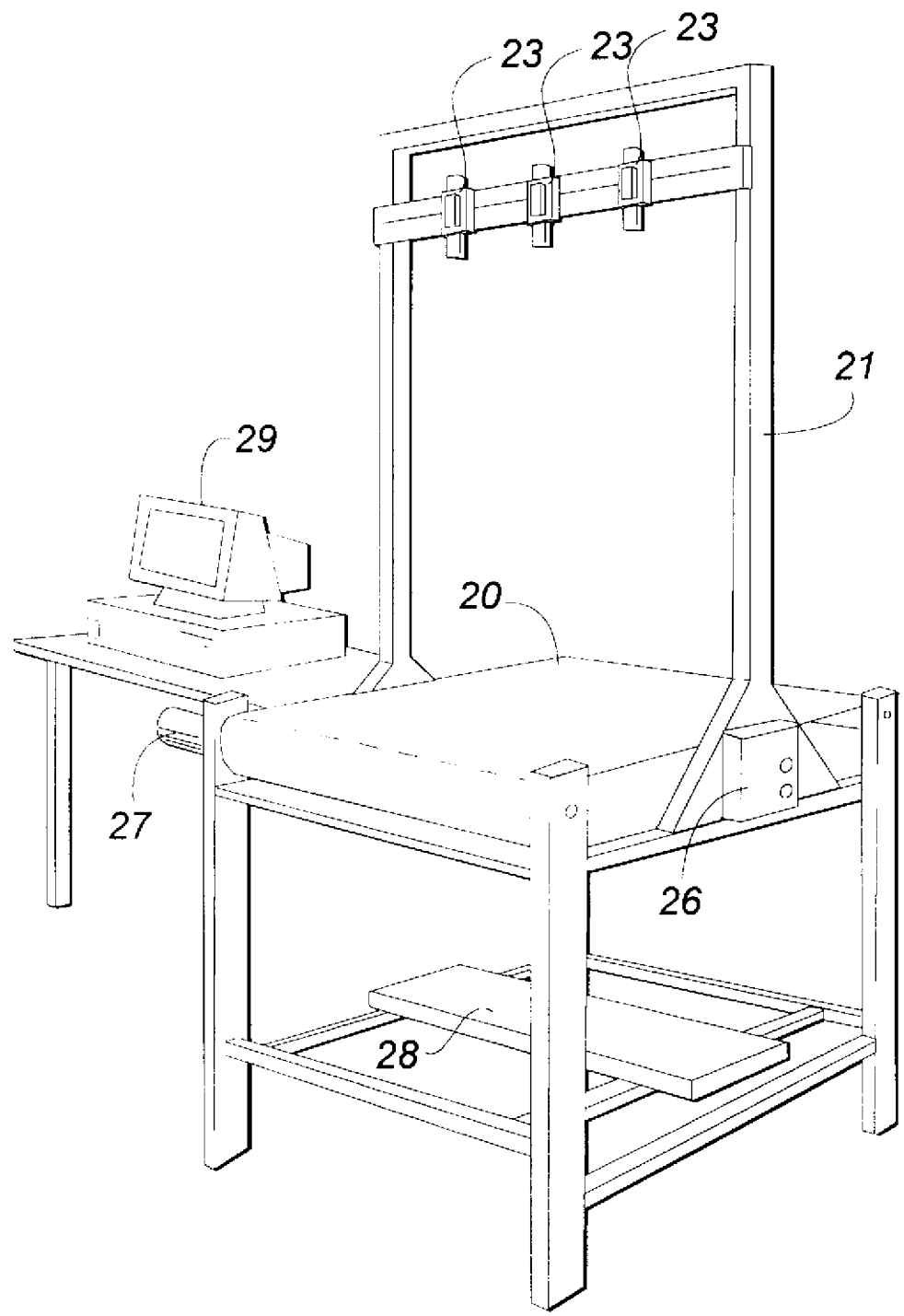
FIG. 15 illustrates a preferred embodiment of the FDI system of the present invention for detecting defects in textile fabrics.

FIG. 15 illustrates a preferred embodiment wherein the FDI system of the present invention is incorporated into an actual loom for detecting and identifying defects of the type defined above in textile fabrics being manufactured. It will be apparent to those skilled in the art that the FDI system of the present invention can be disposed at virtually any location along the loom provided that the location is suitable for capturing an image of the textile fabric being manufactured. In accordance with the preferred embodiment, one CCD array camera 23 is fixedly mounted to a frame 21 every 12 to 15 inches of fabric width. The frame 21 is connected to the loom such that the cameras 23 are disposed to capture images of the fabric 20 being manufactured by the loom. A light source 28 is preferably, but not necessarily, positioned so that the fabric being manufactured is interposed between the light source 28 and the cameras 23. The fabric is moved along the loom by fabric motion motor 27 which receives control signals from fabric motion drive control 26. A computer 29 is coupled to the cameras 23 and to the loom control system (not shown) for obtaining images captured by the cameras 23 and for performing the fractal scanning technique and the fuzzy wavelet analysis of the present invention to detect and identify defects in the fabric 20. The computer 29 controls the manufacturing process in accordance with the types of defects identified to eliminate or minimize defects. The computer 29 preferably contains a Pentium™ processor, but may also contain other types of microprocessors as well as parallel processors. The computer 29 preferably is equipped with a frame grabber card for receiving and storing digital representations of the images captured by each of the cameras 23 in memory inside computer 29. The computer 29 multiplexes among the outputs of cameras 23 so that each of the images captured by each of the cameras 23 is separately analyzed. Each camera 23 looks at one particular area of the fabric 20 so that the combination of the images captured by the cameras 23 make up a full image of the fabric 20. If defects are detected over corresponding scan lines in at least two cameras, the FDI system of the present invention determines that a defect has occurred and proceeds to identify the type of defect.

In accordance with the preferred embodiment, the CCD array cameras 23 are operating in the visible spectrum. The light source 28 preferably comprises four standard fluorescent light bulbs. A diffuser (not shown) disposed between the light source 28 and the fabric 20 provides uniformity in the light being projected on the fabric 20. A television monitor (not shown) can also be coupled to the cameras 23 so that an operator can view the images being captured by the cameras 23. The intensity of the light source 28 can be adjusted by the operator to optimize the images being captured by the cameras 23. A diffuser is chosen based on the type of fabric being inspected to obtain optimum illumination. Also, the portion of the loom proximate the FDI system of the present invention is preferably within an enclosure so that the lighting of the FDI system is closely controlled and noise from other light sources is eliminated or minimized.

In accordance with the preferred embodiment, the CCD array cameras preferably are Polaris Industries Model VT 90D industrial quality high resolution black and white CCD cameras. The Model VT 90D has a resolution of 811 (H)×508 (V) pixels and an image area of 7.95 mm×6.45 mm. The horizontal frequency is 15.734 kHz and the vertical frequency is 60 kHz. The television monitor preferably is a Toshiba monochrome black and white Model TVM 1001 with a 10 inch screen. The frame grabber preferably is a Microdisc, Inc. monochrome frame grabber, Model OC-TCXO-MXD10.

Figure 16:
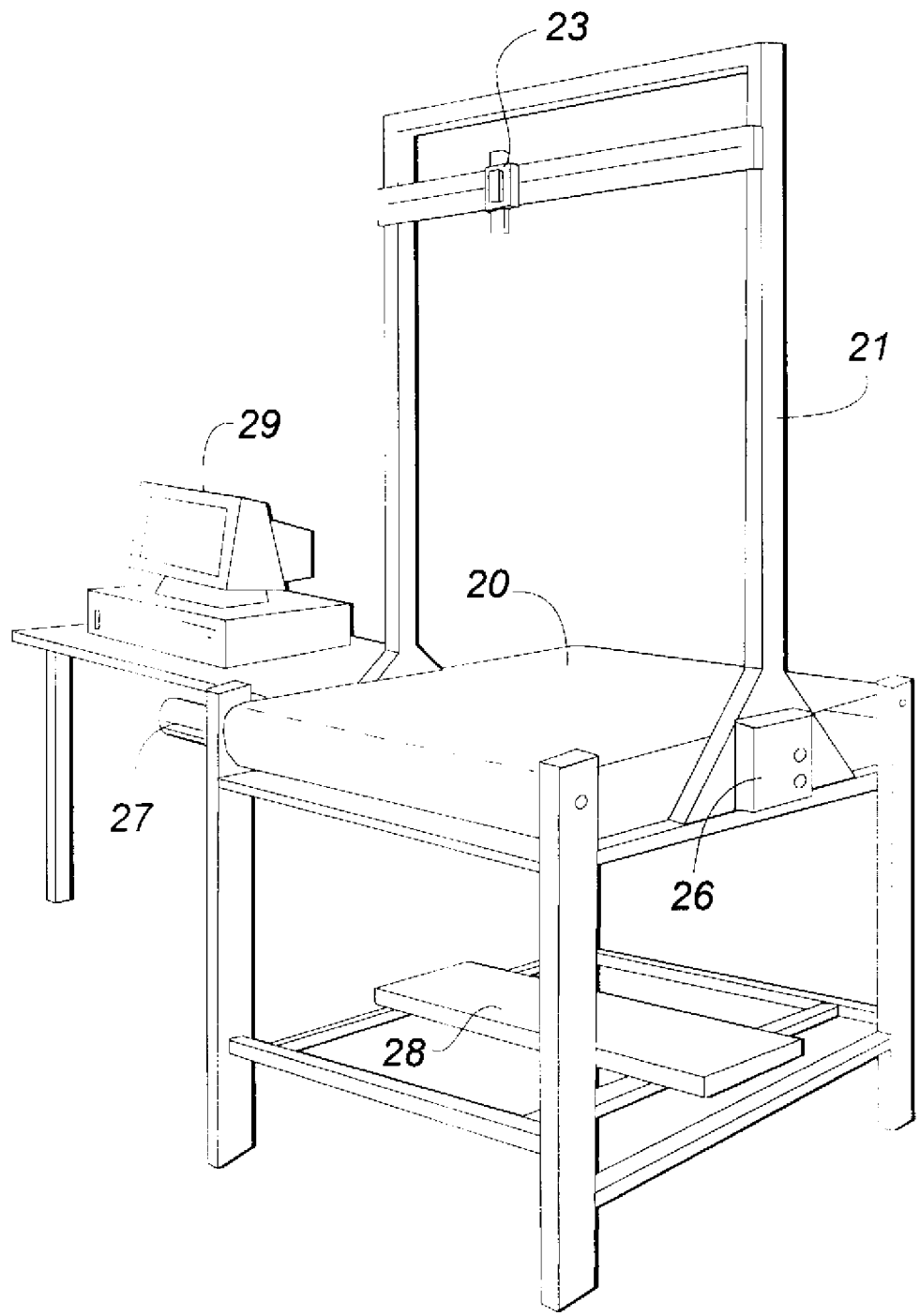
FIG. 16 illustrates an alternative embodiment of the FDI system of the present invention for detecting defects in textile fabrics.

FIG. 16 is an alternative embodiment of the present invention wherein the image sensor 23 is a line scan camera preferably comprising 7,000 pixels arranged in one line, preferably transverse to the movement of the fabric 20. Therefore, only one line of pixels is being used to scan the image. In order to construct a 2-D image with the line scan camera, several lines must be accumulated. However, by accumulating the line scans to build the full image, a higher resolution image is obtained due to the higher resolution of the line scan camera as compared to the CCD array cameras. Once the full image has been obtained, the image is processed to detect and identify defects in the fabric. The processing of the image obtained in accordance with the embodiment of FIG. 16 is essentially the same as the processing of the image obtained in accordance with the embodiment of FIG. 15, with the exception that the frame grabber is unnecessary in the embodiment of FIG. 16.

Figure 17:
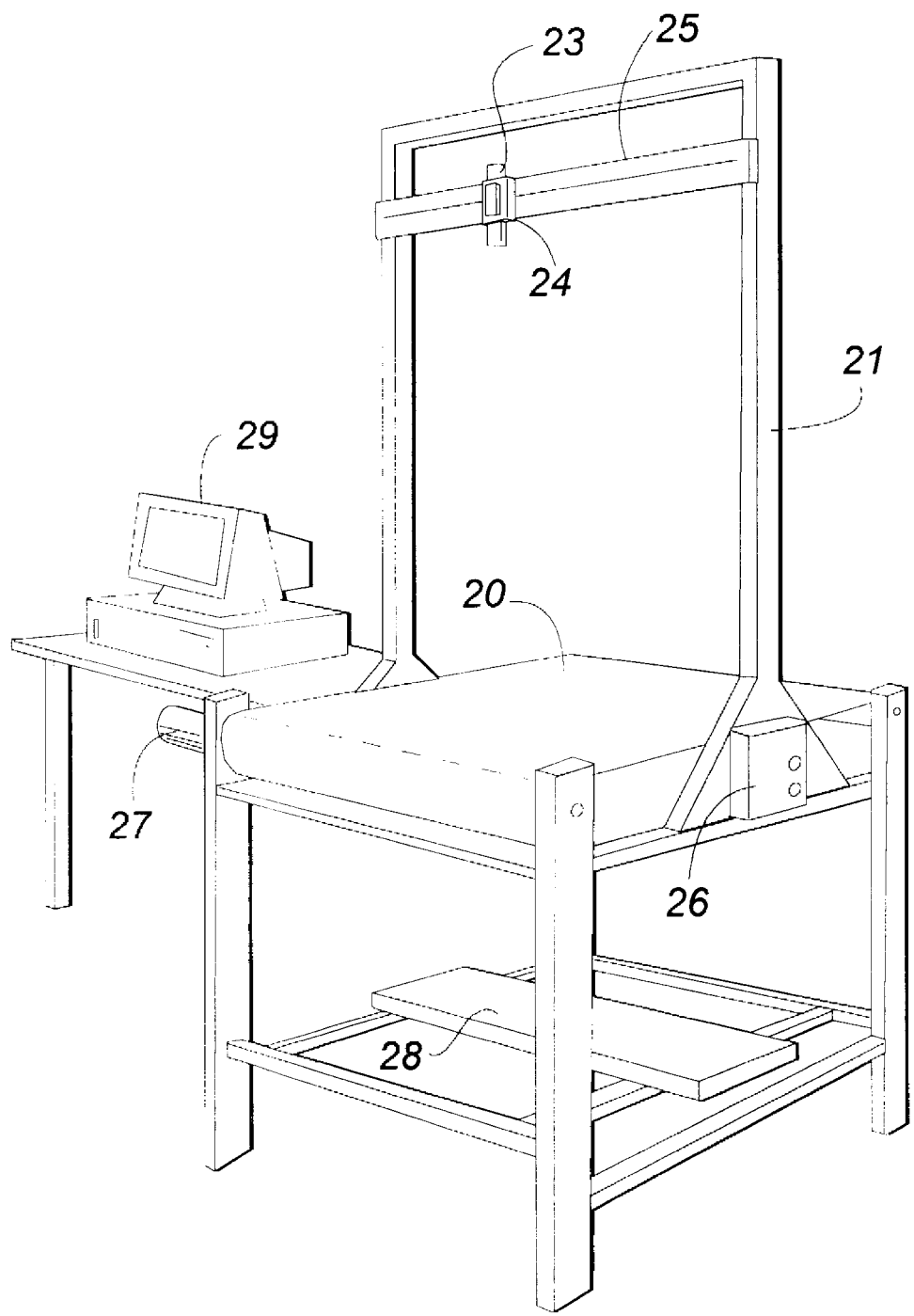
FIG. 17 illustrates an alternative embodiment of the FDI system of the present invention for detecting defects in textile fabrics.

FIG. 17 illustrates another embodiment of the present invention wherein the sensor array 23 is a CCD array camera movably secured to a linear drive 25 via a linear drive stepper motor 24. A stepper motor controller (not shown) is connected to computer 29 and to stepper motor 24 for receiving control signals from computer 29 and for delivering pulses to stepper motor 24 for moving CCD array camera 23 in the longitudinal direction along linear drive 25. A linear slide end-of-travel switch (not shown) is located at each end of linear drive 25 for communicating with computer 29 to enable computer 29 to determine the location of CCD array camera 23 along the linear drive 25. A fabric travel encoder (not shown) comprised in the fabric motion drive control 26 communicates with computer 29 to enable the computer 29 to determine the coordinates of the area of the fabric 20 being captured by CCD array camera 23. In all other respects, the embodiment of FIG. 17 is identical to the embodiments of FIGS. 15 and 16.

Although the embodiments discussed above preferably utilize a light source which produces visible light, it will be apparent to those skilled in the art that other frequencies of light which are not in the visible spectrum can also be used. For example, cameras are available which operate in the infrared spectrum. By using infrared light instead of visible light, some sources of noise can be eliminated so that placing the FDI system in an enclosure may be unnecessary. It is also possible to use other frequencies of light to analyze only the texture of the fabric rather than the color. For example, where the fabric being inspected contains a printed pattern, it is more beneficial to look at the texture of the fabric rather than the color. In this case, it is desirable to use a frequency of light, or a range of frequencies of light, which allow the color of the fabric to be ignored. Therefore, the present invention is not limited to using any particular frequency of light. Similarly, the present invention is not limited to using any particular type of image sensor for obtaining an image of the fabric or to any particular physical arrangement for disposing the image sensor in proximity to the fabric for reading the image. It will be apparent to those skilled in the art that virtually any type of image sensor, light source and means for locating the image sensor and light source along the loom can be used as long as a satisfactory image of the fabric being inspected can be obtained. Furthermore, the present invention is not limited to inspecting any particular types of fabric or to any particular type of fabric manufacturing process. For example, the FDI system of the present invention is suitable for inspection of griege fabrics, and fabrics manufactured by other methods, such as warp knitting, circular knitting, etc.

Figure 18:
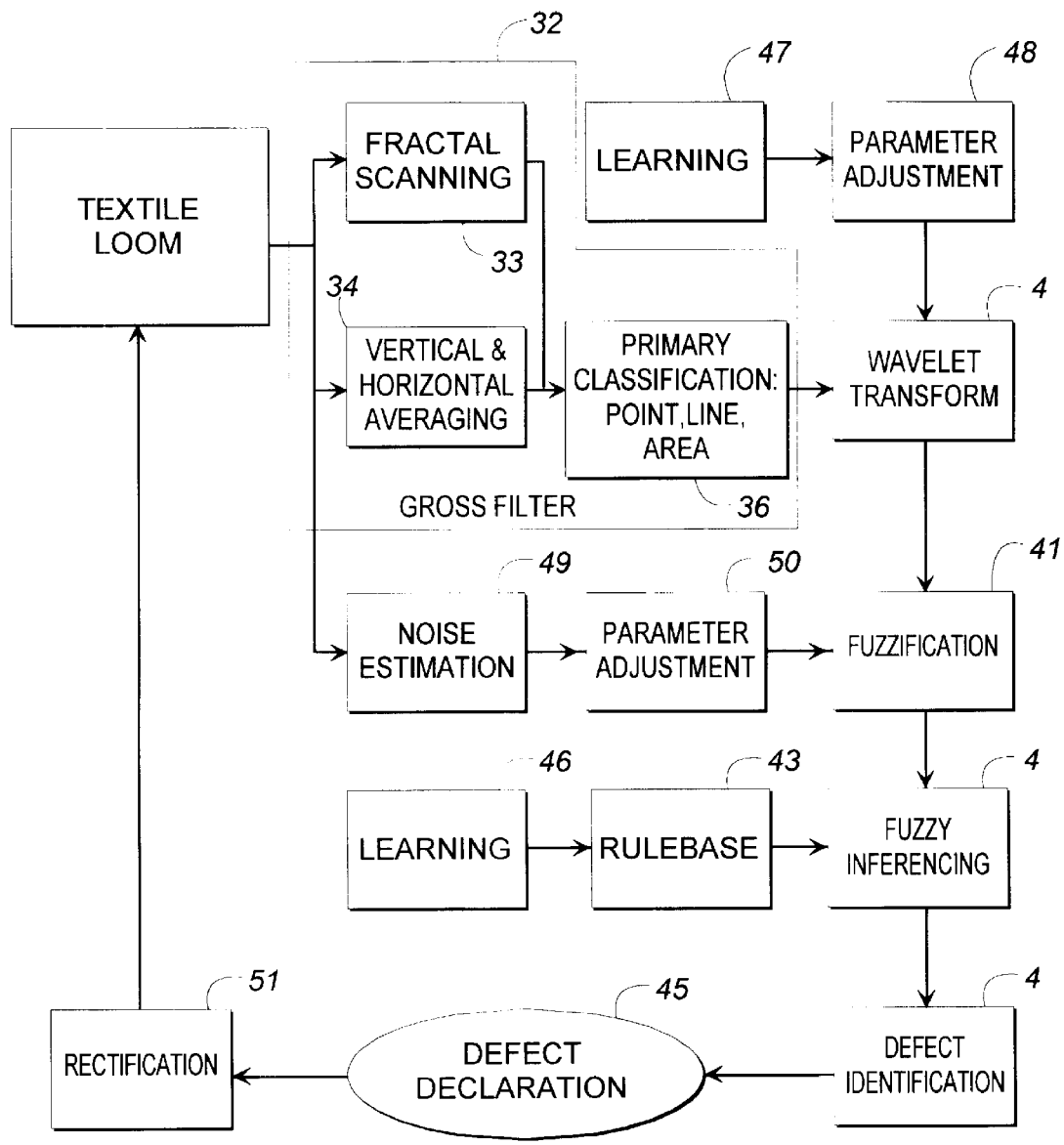
FIG. 18 illustrates a block diagram of the FDI system of the present invention in accordance with the preferred embodiment.

The processing of the image of the fabric to detect and identify defects will now be discussed with respect to FIGS. 18–22. FIG. 18 is a block diagram of the FDI system of the present invention in accordance with the preferred embodiment. The system works in two hierarchial levels. The first level is the gross filter stage 32 which detects the presence of the fault or defect. The gross filter stage 32 consists of fractal scanning 33, vertical and horizontal averaging 34 and primary classification 36 into one of the broad categories of line point and area defects. Fractal scanning has already been discussed in detail above. Vertical and horizontal scanning consists of scanning 10 to 15 lines at regular intervals and averaging them. Since the FDI process of the present invention may be constrained by time limits (e.g., when being implemented on-line), both of the above scanning techniques help to reduce data and hence processing time. If the gross filter 32 detects a fault (or possible fault), the processing is handed over to the FWA analysis which classifies the fault into one of the anticipated faults or no fault, as the case may be.

The second level is the fine filter stage which utilizes the information from the gross filter stage to identify the defects using the FWA of the present invention. The fine filter stage includes wavelet transform 40, fuzzification 41, fuzzy inferencing 42, rule base 43, defect identification 44, defect declaration 45, off-line learning 46, on-line learning 47, parameter adjustment 48 and 50A, noise estimation 49 and rectification 51. Rectification closes the loop and, based on the defect that has been classified, recommends corrective steps that need to be taken to correct the manufacturing process to eliminate the types of defects that are occurring. Since all of these elements of the FDI system of the present invention have been discussed in detail above, a detailed discussion of them will not be provided here. Attached as Appendix A is a printout of the source code of the present invention in C which controls the software components of the FDI system of the present invention shown in FIG. 18.

Figure 19:
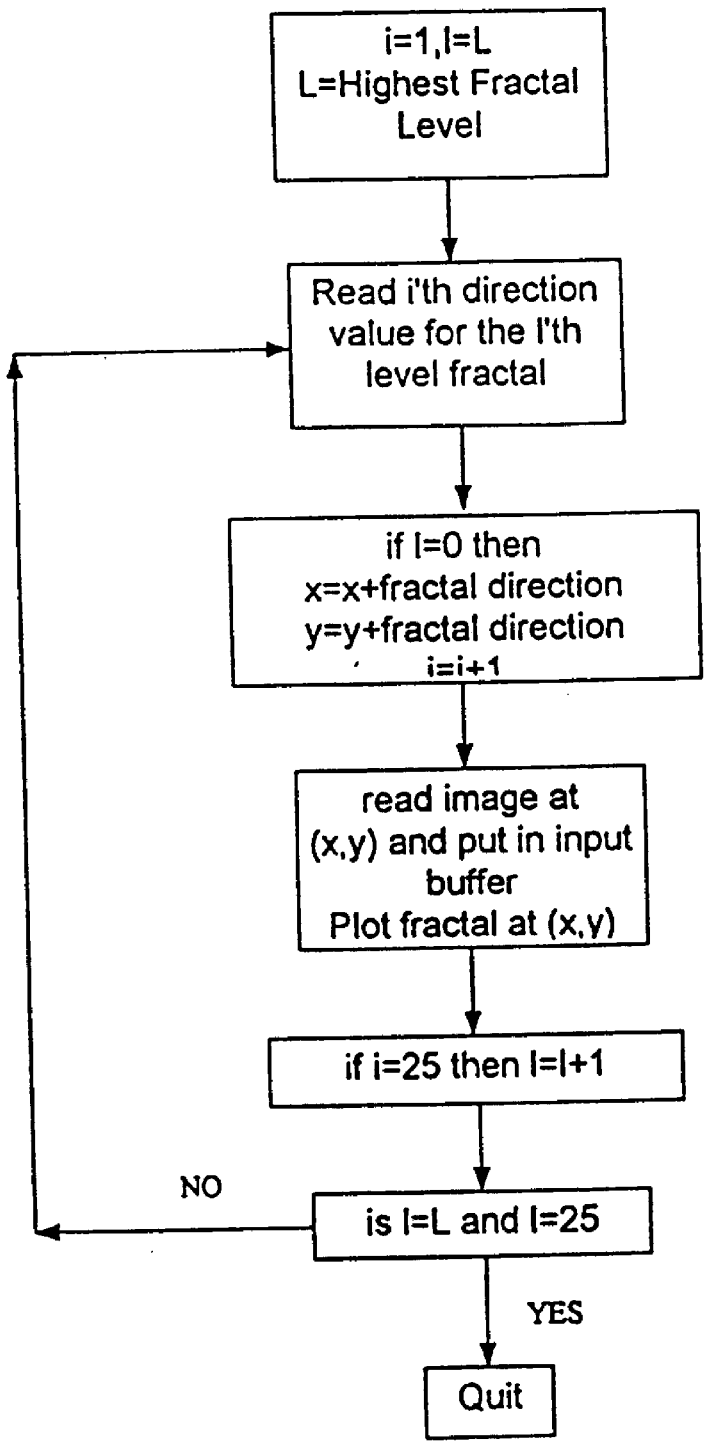
FIG. 19 is a flow chart of the fractal scanning process of the present invention in accordance with the preferred embodiment.

FIG. 19 is a flow chart of the fractal scanning technique implemented by the present invention in accordance with the preferred embodiment. In accordance with the preferred embodiment, the number of subfractals i in one fractal is 25 and the total number of levels of fractals in the nested hierarchy is also 25. The basic fractal preferably has one of the four orientations depicted in FIG. 6 and discussed above. Once 25 subfractals of the image have been read (i=25), the level of the fractal l is incremented by 1. Once 25 subfractals (i=25) in the 25th fractal (l=25) have been scanned, the fractal scanning routine is complete as indicated by the block labeled "Quit" in FIG. 19. The fractal level l only gets incremented after 25 subfractals in the particular fractal have been scanned. As long as i has not been incremented to 25, the routine continues determining the x and y coordinates of the next subfractal and reading the corresponding image at those coordinates. After 25 subfractals have been obtained, i.e., i=25, the subfractal counter is reset to zero and the level of the fractal l is increased by one. It will be apparent to those skilled in the art that the fractal orientation, the number of subfractals contained in the basic fractal, and the maximum fractal level can be selected in accordance with the application, virtually without restriction.

Figure 20:
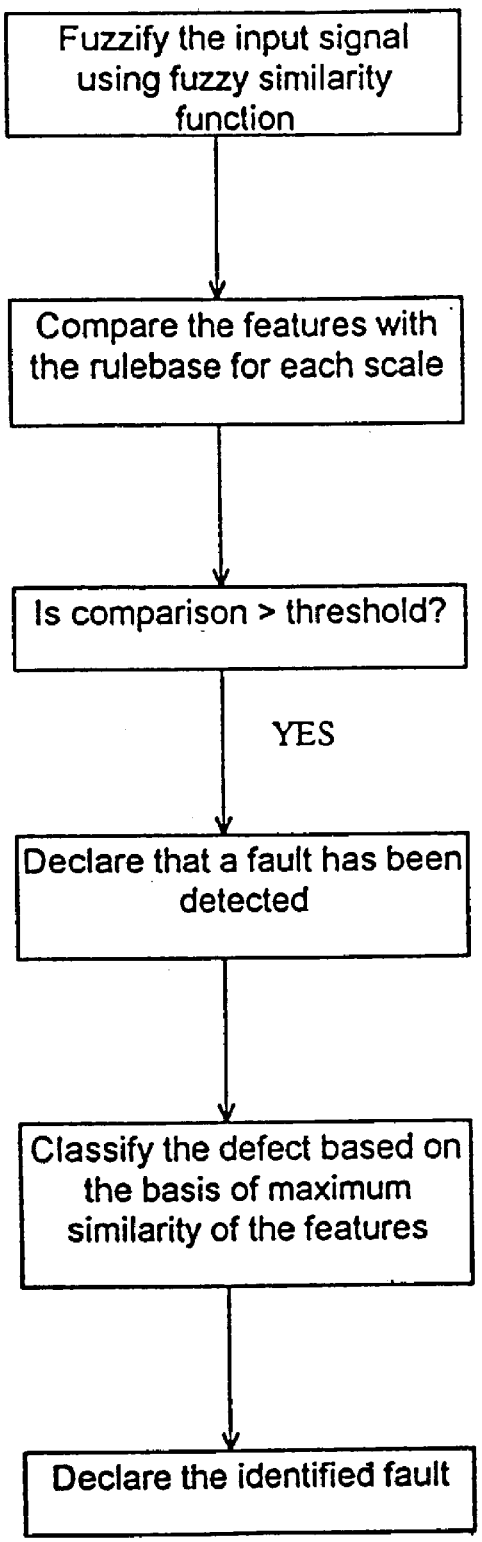
FIG. 20 is a flow chart showing fuzzification, fuzzy inferencing, defect detection and defect declaration in accordance with the present invention.

FIG. 20 is a flow chart generally illustrating the fuzzification process 41, the fuzzy inferencing process 42, the defect identification 44 and the defect declaration 45. Since these components of the present invention have been discussed in detail above, a detailed discussion of them will not be provided here. In general, the fuzzification module 41 calculates the degree of membership of the features extracted during the wavelet transformation process 40 with templates from the knowledge base to form fuzzy sets. The fuzzy inferencing engine 42 utilizes if-the a defect has been observed. The degree of similarity between the extracted features and the corresponding template in the knowledge base is then obtained to determine the type of defect which has occurred.

Figure 21:
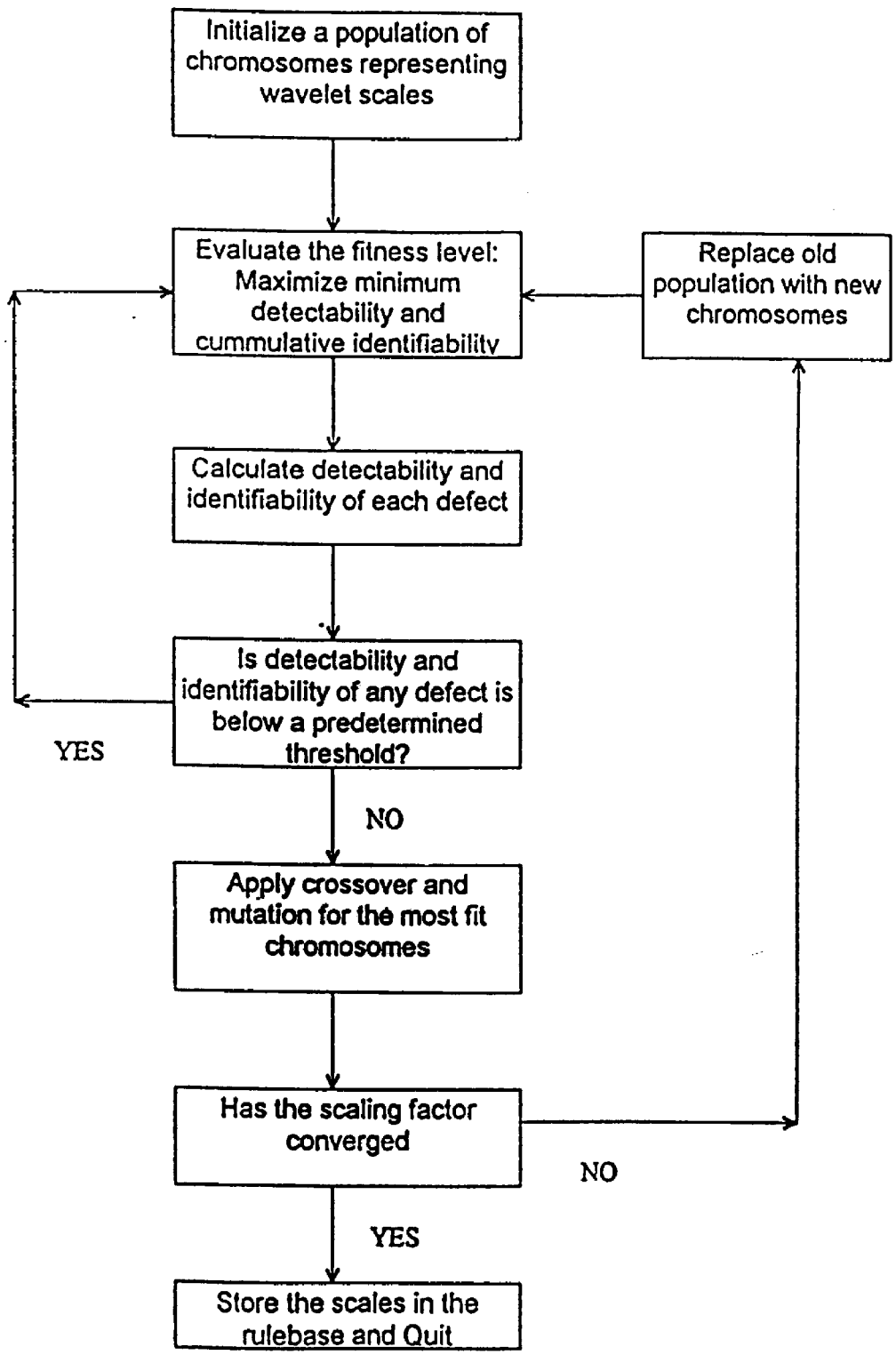
FIG. 21 is a flow chart of the genetic algorithm of the present invention implemented by the off-line learning module.

FIG. 21 is a flow chart of the genetic algorithm utilized by the present invention to create the rule base component 43. The genetic algorithm is discussed in detail above under the heading "Off-Line Learning Using a Genetic Algorithm".

Figure 22:
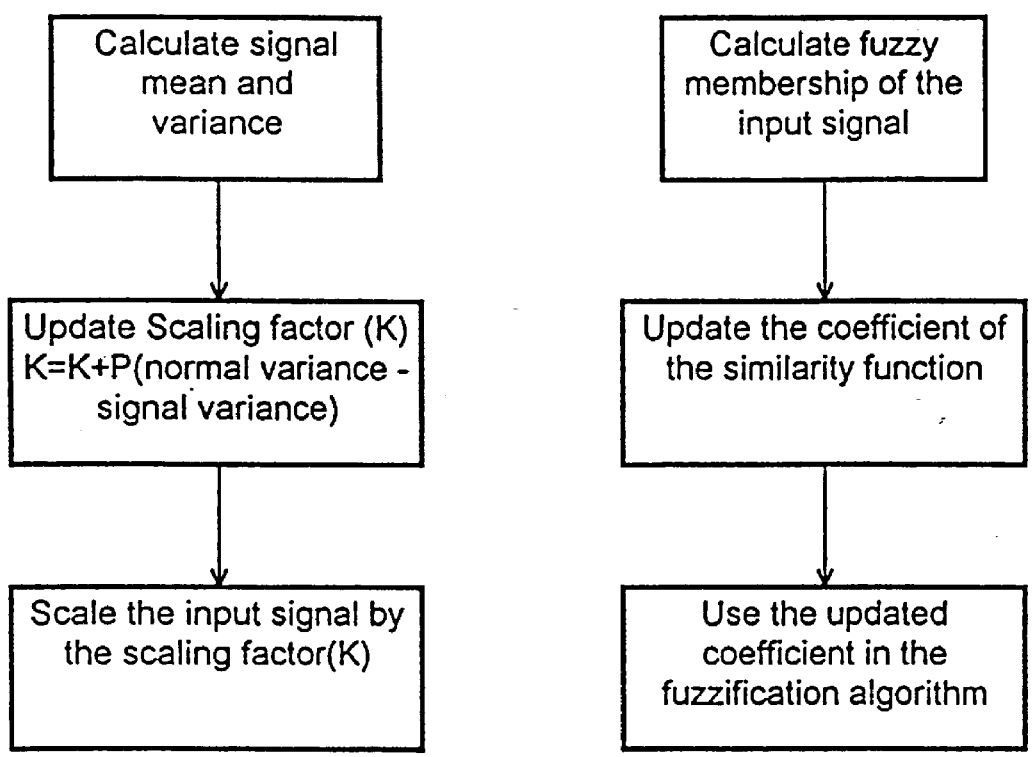
FIG. 22 is a flow chart of the on-line learning module of the present invention.

FIG. 22 is a flow chart of the on-line learning module 47 and the parameter adjustment module 48 shown in FIG. 18. These modules are discussed in detail above under the heading "On-Line Learning".

In an experiment conducted with the present invention, the FWA algorithm was tuned to detect and identify the following defects: (1) broken pick; (2) coarse end; (3) double end; (4) end out; (5) harness drop; (6) knot; (7) oily spot; (8) stub; (9) start mark; and (10) woven in waste. A space search for values of scale from 0.01 to 0.82 was conducted for detectability and identifiability and the detectability of all the defects were found to drop around a scale of 0.02. This is the scale at which the texture of the fabric under inspection becomes more dominant. The detectability was found to be fairly uniform over a wide range of scales from 0.05 to 0.07. Identifiability, on the other hand, varies from one defect to another. It was found to be more erratic near the scale of 0.02 and much more uniform in most other regions.

Figure 23:
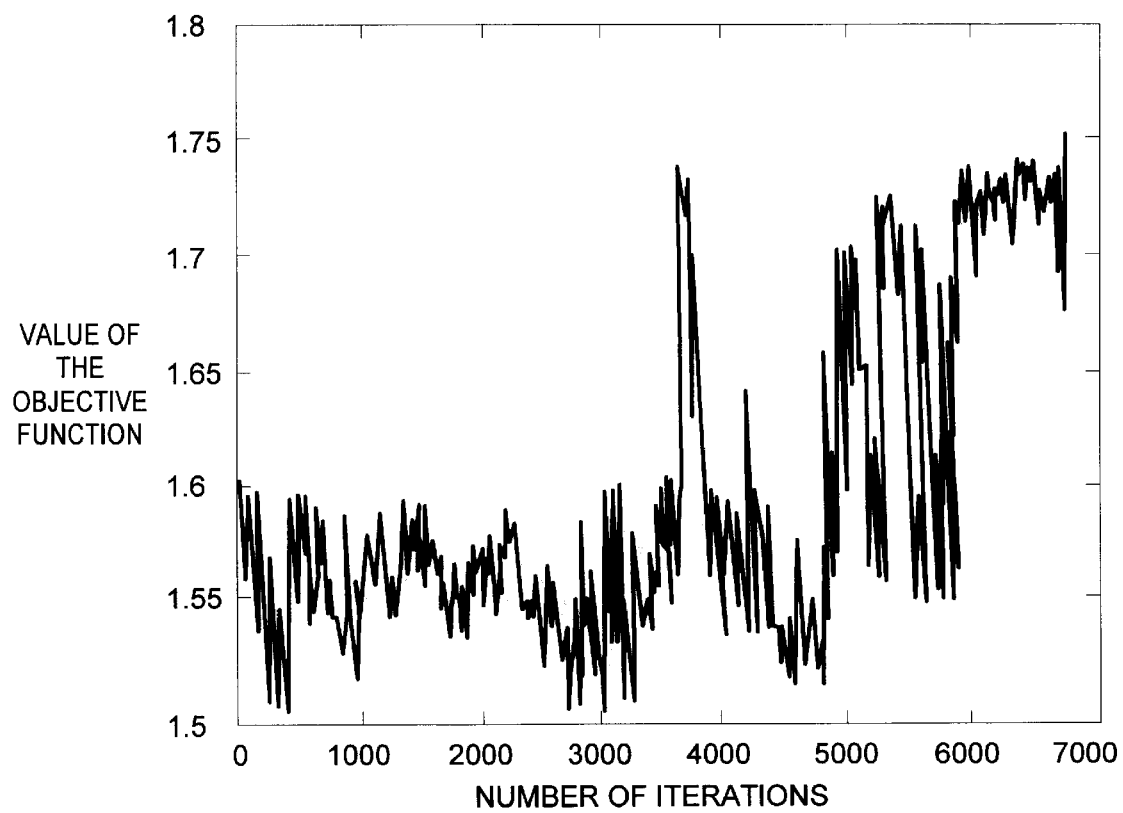
FIG. 23 graphically illustrates the convergence of the objective function in accordance with the learning process of the present invention.

The learning process was implemented on MATLAB for five wavelet scales. The convergence of the objective function is shown in FIG. 23. The values of the scales returned by this optimization were {0.4144, 0.1544, 0.6739, 0.7526, 0.2222}.

Figure 24:
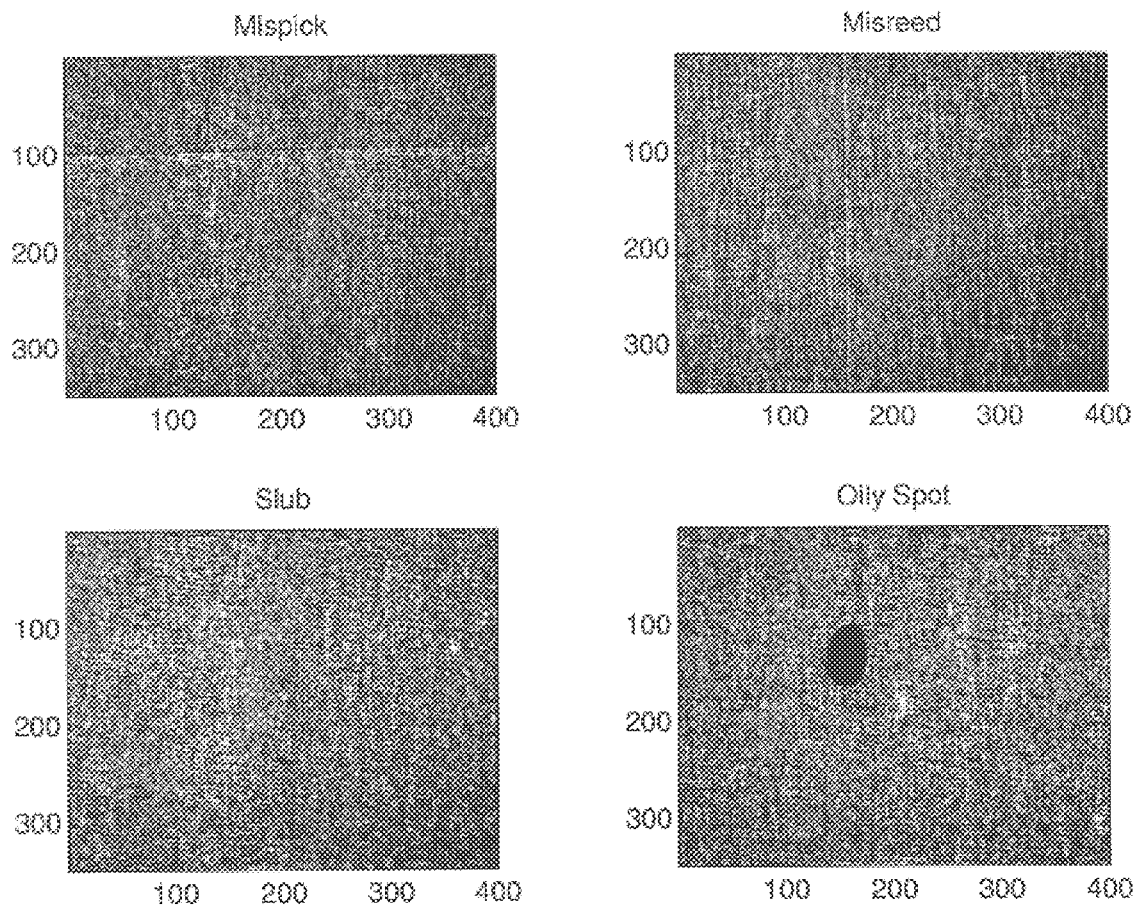
FIG. 24 shows certain types of defects in textile fabrics detected during an experimental run of the present invention.
Figure 25:
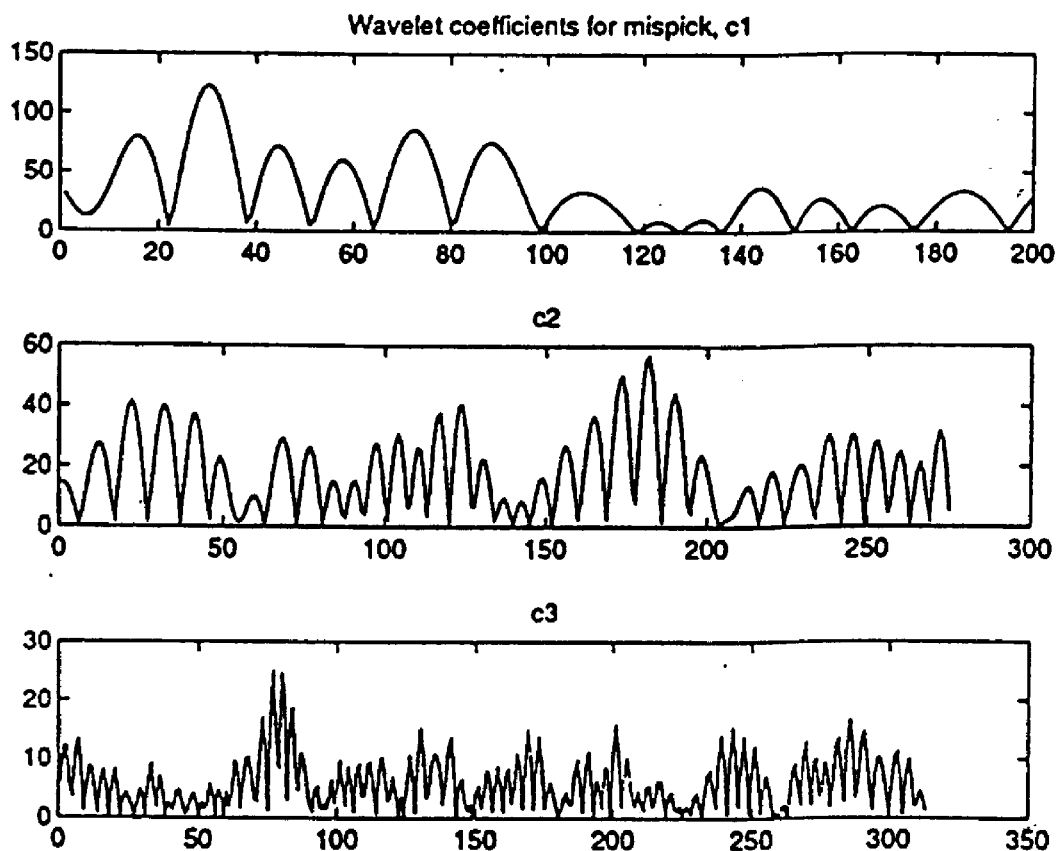
FIGS. 25–28 illustrate wavelet coefficients used during the experimental run to detect defects.
Figure 26:
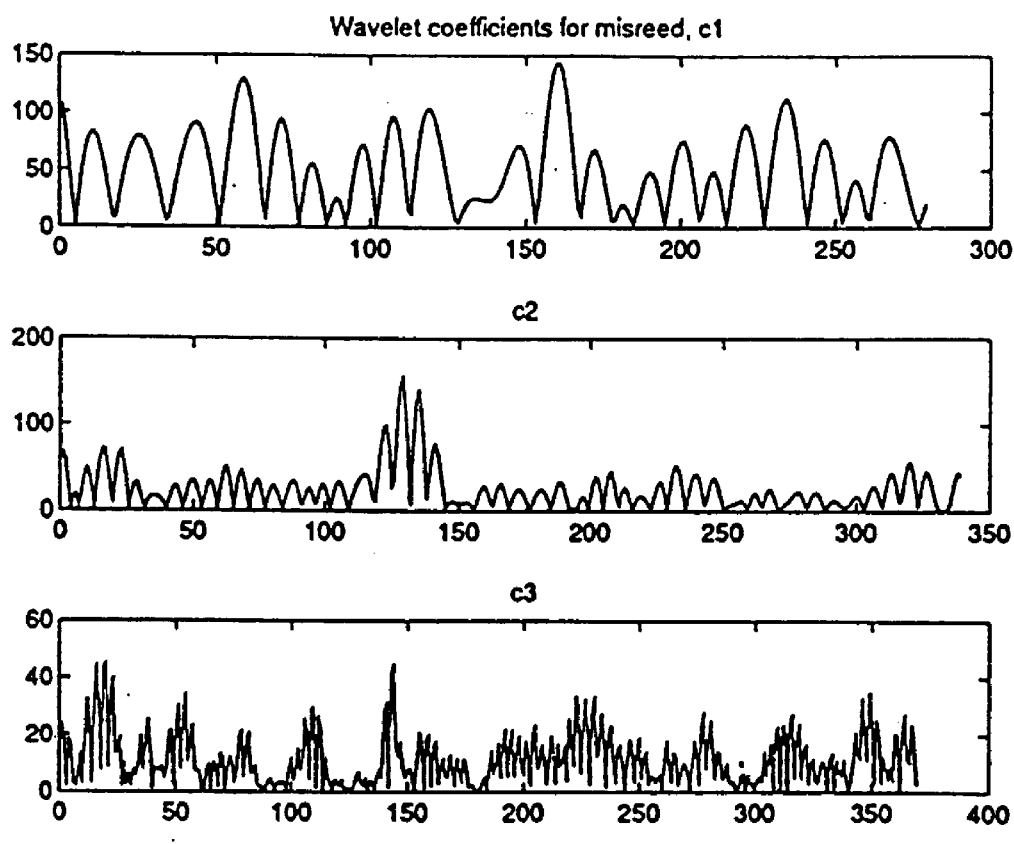
Figure 27:
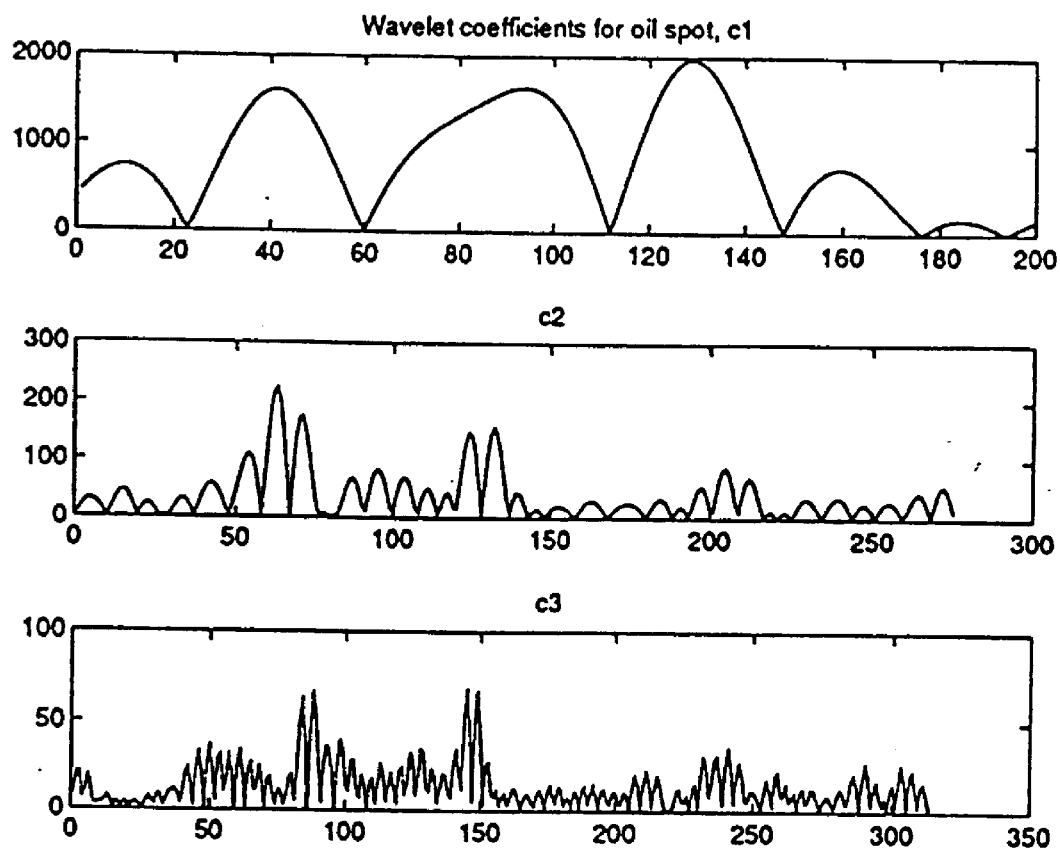
Figure 28:
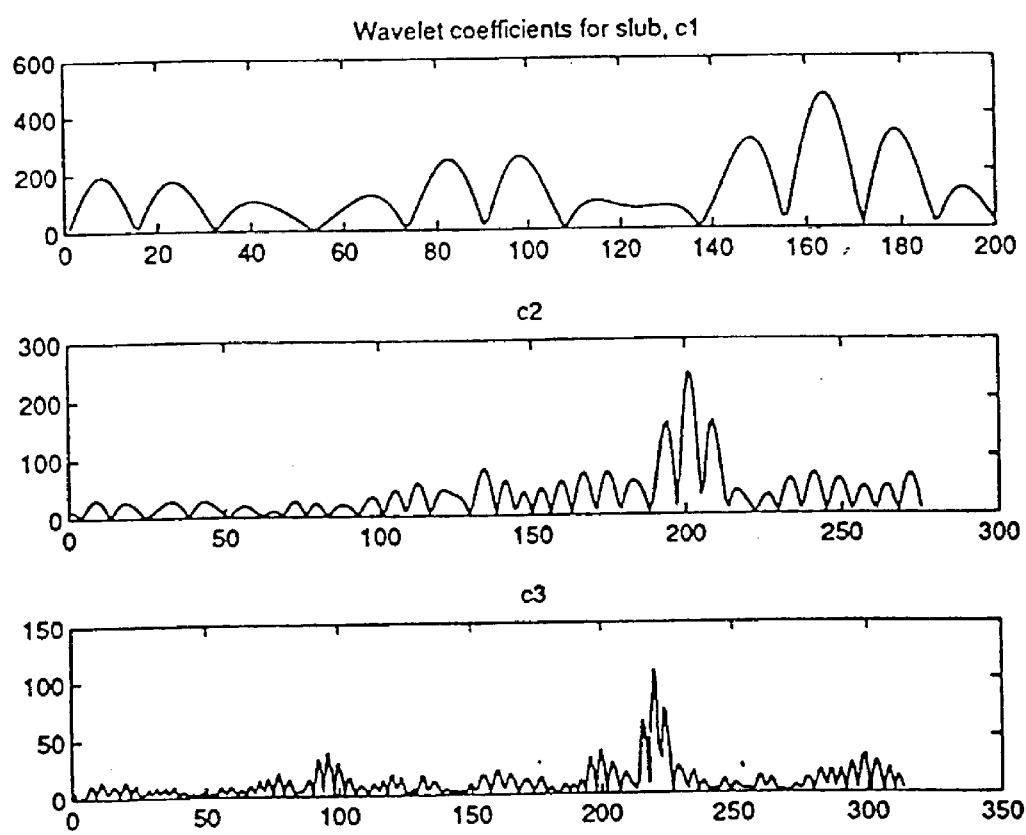

The defects given here as an example are mispick, misreed, oil spot and slub. These defects are shown in FIG. 24. The corresponding wavelet coefficients for scales of a=0.1544, 0.4144, 0.07526 are labeled c1, c2, c2 and are shown in FIGS. 25, 26, 27 and 28. It is seen that certain wavelet functions are more sensitive to some fault features as compared to others. The learning mechanism optimizes this for the classification process. Since the textile structure is periodic in nature, it is also important to avoid scales which respond to the inherent frequencies of the fabric.

The results of the experimental run are enumerated in FIG. 29. This provides for the creation of a defect map on the entire length of fabric. False Alarm (FA) indicates cases where the algorithm falsely declared a defect, while the cases in which a defect was detected but incorrectly classified are indicated by False Identification (FI).

Although the present invention has been described with respect to particular embodiments, it should be apparent to those skilled in the art that the present invention is not limited to those embodiments. For example, scanning algorithms other than the preferred algorithm discussed above may be suitable for use with the FDI system of the present invention. It will also be apparent to those skilled in the art that, although the preferred transform is the wavelet transform, other types of transforms, such as, for example, the Fourier Transform, can also be used with the FDI system of the present invention depending on the range of frequencies over which the defects are expected to occur, and depending on whether the signal is stationary or non stationary. It is desirable to use the wavelet transform or some other type of transform which provides an analysis which is localized in both the frequency and time domains where the defects are occurring over a wide range of frequencies or where the input signal is nonstationary. The wavelet transform merely is the preferred transform because it is localized in both frequency and time. It should also be clear that the FDI system of the present invention is not limited to detecting defects in textile fabrics but that it may also be used for detecting and identifying other types of defects in other types of products or materials, e.g., paper, glass, food, metals, lumber, etc.

What is claimed is:

1. An apparatus for analyzing an image to detect and identify defects in an object, said apparatus comprising:
    at least one image sensor disposed to capture an image of the object;
    a light source for projecting light onto the object;
    means for converting the captured image into a digital representation;
    a storage device for receiving the digital representation of the image from said means for converting the captured image and for storing the digital representation; and processing means for processing the digital representation of the captured image stored in said storage device, wherein the processing comprises a convolution operation on the digital representation whereby one or more wavelets are used to transform the input digital signal into wavelet coefficients thus extracting certain defect feature sets from the digital representation, performing fuzzification by calculating the degree of membership of the extracted feature sets in feature templates stored in a knowledge base in said storage device in accordance with a similarity function, generating fuzzy sets from said defect feature sets if their degree of membership exceeds a threshold, and performing fuzzy inferencing with said rules and fuzzy sets to classify the type of defect that has occurred.

2. An apparatus according to claim 1 wherein prior to performing the transformation, a horizontal, a vertical and a fractal scanning technique are performed on the digital representation to convert the digital representation into several 1-D digital representations.

3. An apparatus according to claim 2 wherein said at least one image sensor is comprised of two or more CCD array cameras, and wherein each CCD array camera captures an image of a different area of the object and wherein a defect is determined to exist when a defect is detected in corresponding scan lines of at least two of said CCD array cameras.

4. An apparatus according to claim 3 wherein the object is a fabric comprising one of a griege fabric, a textile fabric being manufactured on a loom, a textile fabric being manufactured by warp knitting, and a textile fabric being manufactured on a circular loom.

5. An apparatus according to claim 2 wherein said at least one image sensor is comprised of a line scan camera and wherein a full image of the object is obtained by producing relative motion between said line scan camera and the object and by accumulating line scans to obtain a full image of the object and wherein the full image is then analyzed to determine whether a defect exists and, if so, the type of defect.

6. An apparatus according to claim 5 wherein the object is a fabric comprising one of a griege fabric a textile fabric, being manufactured on a loom, a textile fabric being manufactured by warp knitting and a textile fabric being manufactured on a circular loom.

7. An apparatus according to claim 1 wherein said at least one image sensor is comprised of two or more CCD array cameras, and wherein each CCD array camera captures an image of a different area of the object and wherein a defect is determined to exist when a defect is detected in corresponding scan lines of at least two of said CCD array cameras.

8. An apparatus according to claim 1 wherein said at least one image sensor is comprised of a line scan camera and wherein a full image of the object is obtained by producing relative motion between said line scan camera and the object and by accumulating line scans to obtain a full image of the object and wherein the full image is then analyzed to determine whether a defect exists and, if so, the type of defect.

9. An apparatus according to claim 1 wherein the object is a fabric comprising one of a griege fabric, a textile fabric being manufactured on a loom, a textile fabric being manufactured by warp knitting, and a textile fabric being manufactured on a circular loom.

10. An apparatus according to claim 1 wherein said light source produces only infrared light and wherein said at least one image sensor is an infrared camera.

11. An apparatus according to claim 1 further comprising a light diffuser disposed between said light source and the object for controlling the uniformity and intensity of the light being projected onto the object.

12. A method for detecting and identifying defects in an object comprising the steps of:

storing the digital representation of the image in memory;

transforming the digital representation by performing a transformation process which extracts certain defect feature sets contained in the image of the object; the transforming step including convolving the digital representation with a series of wavelets; wherein the resulting wavelet coefficients comprise the defect features; creating fuzzy sets by calculating the degree of membership of the extracted features with stored feature templates according to a similarity function; and using the fuzzy sets in a fuzzy inferencing scheme to infer and classify whether a defect has been detected and, if so, the type of defect that has occurred; wherein the fuzzy wavelet coefficients are compared with fuzzy sets stored as representative features in a knowledge base for different wavelet scales and for a plurality of anticipated defects and wherein the wavelet scales are selected to maximize detectability and identifiability measures.

13. The method of claim 12 wherein the step of selecting the wavelet scales is accomplished by using a genetic algorithm.

14. The method of claim 12 further comprising an on-line learning process which is accomplished by obtaining statistical information relating to said image and by scaling said image by a factor determined in accordance with the statistical information.

15. A method according to claim 12 wherein a horizontal, a vertical and a fractal scanning technique are performed on the digital representation stored in memory to convert the digital representation into several 1-D digital representations.

16. An apparatus for analyzing an image of a fabric to detect and identify defects in the fabric, said apparatus comprising:

at least one image sensor disposed to capture the image of at least part of the fabric;

a light source for projecting light through the fabric;

means for converting the captured image into a 2D digital representation;

a storage device for receiving said 2D digital representation of the image from said converting means and for storing said digital representation; and processing means for processing said 2D digital representation of the captured image, said processing means including means for converting said 2D digital representation into at least one ID scan of the image which is particularly adapted to detect an expected defect type, means for convolving said at least one 1D scan of said image with at least one predetermined wavelet from a firmly of wavelets to extract certain defect features in the form of wavelet coefficients from said at east one 1D digital representation means for concerting said wavelet coefficients into fuzzy sets via a similarity transformation, and means for declaring and classifying defects based upon said defect features.

17. An apparatus for analyzing an image as set forth in claim 16, wherein said apparatus further comprises;

means for preprocessing said image to improve the defect signature contrast with respect to background noise.

18. An apparatus for analyzing an image as set forth in claim 16, wherein said apparatus further comprises:
   means for on-line learning which adjusts the defect feature detection parameters of the apparatus based upon measured variables of the process in real time.

19. An apparatus for analyzing an image as set forth in claim 18, wherein said on-line learning means further includes:
   means for modifying the wavelet parameters.

20. An apparatus for analyzing an image as set forth in claim 18, wherein said on-line learning means further includes:
   means for modifying the fuzzy membership function parameters.

21. An apparatus for analyzing an image as set forth in claim 16, wherein said apparatus further comprises:
   means for off-line learning which adjusts one of the detection and classification parameters of the apparatus based upon the measured variables of the process.

22. An apparatus for analyzing an image as set forth in claim 21, wherein said off-line learning means further includes:
   means for modifying the fuzzy defect rules.

23. An apparatus for analyzing an image as set forth in claim 16, wherein said apparatus further includes:
   means for estimating the noise in the image and for adjusting one of the detection and classification parameters of the apparatus based on the measured noise.

24. An apparatus for analyzing an image as set forth in claim 16, wherein said means for converting said 2D digital representation further includes:
   means for horizontally scanning said 2D digital representation which is adapted for sensitivity to fabric warp defects;
   means for vertically scanning said 2D digital representation which is adapted for sensitivity to fabric filling defects; and
   means for fractal scanning said 2D digital representation which is adapted for sensitivity to fabric area defects.

* * * * *